(12) United States Patent
Honda et al.

(10) Patent No.: US 8,207,370 B2
(45) Date of Patent: Jun. 26, 2012

(54) PROCESS FOR PRODUCING OPTICALLY ACTIVE BETA-HYDROXY-ALPHA-AMINOCARBOXYLIC ACID ESTER

(75) Inventors: Tatsuya Honda, Takasago (JP); Tatsuyoshi Tanaka, Takasago (JP); Masaru Mitsuda, Takasago (JP)

(73) Assignee: Kaneka Corporation, Osaka (JP)

( * ) Notice: Subject to any disclaimer, the term of this patent is extended or adjusted under 35 U.S.C. 154(b) by 486 days.

(21) Appl. No.: 12/311,325

(22) PCT Filed: Sep. 26, 2007

(86) PCT No.: PCT/JP2007/068629
§ 371 (c)(1),
(2), (4) Date: Mar. 26, 2009

(87) PCT Pub. No.: WO2008/041571
PCT Pub. Date: Apr. 10, 2008

(65) Prior Publication Data
US 2010/0022795 A1    Jan. 28, 2010

(30) Foreign Application Priority Data

Sep. 26, 2006  (JP) ................................ 2006-261107
Nov. 21, 2006  (JP) ................................ 2006-314035

(51) Int. Cl.
C07C 209/50    (2006.01)
C07C 209/46    (2006.01)
C07C 209/00    (2006.01)
C07C 229/06    (2006.01)

(52) U.S. Cl. .......................... 560/170; 564/468; 560/42

(58) Field of Classification Search ........................ None
See application file for complete search history.

(56) References Cited

U.S. PATENT DOCUMENTS 5,525,709 A     6/1996   Davey et al.
2005/0256158 A1* 11/2005 Ghosh et al. ................. 514/313
2006/0167300 A1   7/2006  Hamada et al.

FOREIGN PATENT DOCUMENTS

| JP | 6-80617 | 3/1994 |
|---|---|---|
| JP | 2733583 | 7/1995 |
| JP | 2976214 | 9/1999 |
| JP | 2006-182681 | 7/2006 |
| WO | 2005/005371 | 1/2005 |
| WO | 2005/069930 | 8/2005 |

OTHER PUBLICATIONS

Translation of PCT Written Opinion dated Apr. 4, 2009 in the International (PCT) Application PCT/JP2007/068629 of which the present application is the U.S. National Stage.
International Search Report dated Jan. 8, 2008 in the International (PCT) Application PCT/JP2007/068629 of which the present application is the U.S. National Stage.
Barbara Mohar et al., "Highly enantioselective synthesis via dynamic kinetic resolution under transfer hydrogenation using Ru($\eta^6$-arene)-N-perfluorosulfonyl-1,2-diamine catalysts: a first insight into the relationship of the ligand's $pK_a$, and the catalyst activity", Chem. Commun. 2001, pp. 2572-2573.
Ryoji Noyori et al., "Asymmetric Transfer Hydrogenation Catalyzed by Chiral Ruthenium Complexes", Acc. Chem. Res. 1997, vol. 30, No. 2, pp. 97-102.
Karl-Josef Haack et al., "The Catalyst Precursor, Catalyst, and Intermediate in the Ru$^{II}$-Promoted Asymmetric Hydrogen Transfer between Alcohols and Ketones", Angew. Chem. Int. Ed. Engl. 1997, vol. 36, No. 3, pp. 285-288.

* cited by examiner

*Primary Examiner* — Rosalynd Keys
(74) *Attorney, Agent, or Firm* — Wenderoth, Lind & Ponack, L.L.P.

(57) ABSTRACT

It is an objective of the present invention to produce an anti-form of an optically active β-hydroxy-α-aminocarboxylic acid ester efficiently, simply and industrially advantageously. The objective can be accomplished by directly and selectively producing the anti-form of the optically active β-hydroxy-α-aminocarboxylic acid ester by asymmetric reduction of a β-keto-α-aminocarboxylic acid ester using an optically active amine complex as a catalyst. Further, the β-keto-α-aminocarboxylic acid ester as a raw material can be produced at a high yield by reacting a glycine derivative with a carboxylic acid derivative.

15 Claims, No Drawings

PROCESS FOR PRODUCING OPTICALLY ACTIVE BETA-HYDROXY-ALPHA-AMINOCARBOXYLIC ACID ESTER

TECHNICAL FIELD

The present invention relates to a process for producing an optically active β-hydroxy-α-aminocarboxylic acid ester which is important as a synthesis intermediate for pharmaceutical products, agrochemicals, chemical products and the like. More particularly, the present invention relates to a process for producing an optically active β-hydroxy-α-aminocarboxylic acid ester, especially an anti-form thereof, by asymmetrically reducing a β-keto-α-aminocarboxylic acid ester.

BACKGROUND ART

Conventionally, the following processes is known as a process for producing an anti-form of an optically active β-hydroxy-α-aminocarboxylic acid ester by asymmetric reduction of a β-keto-α-aminocarboxylic acid ester.

(i) A process to synthesize an anti-form by asymmetrically hydrogenating a racemic β-keto-α-aminocarboxylic acid ester with catalytic asymmetric hydrogenation reaction using a ruthenium-optically active phosphine complex catalyst to syn-selectively synthesize an optically active β-hydroxy-α-aminocarboxylic acid ester; and inversing the steric configuration of the hydroxyl group at β-position in the obtained ester (Patent Document 1).

(ii) A process to anti-selectively synthesize an optically active β-hydroxy-α-aminocarboxylic acid ester by asymmetrically hydrogenating a β-keto-α-aminocarboxylic acid ester having no substituent group at the nitrogen atom with catalytic asymmetric hydrogenation reaction using a ruthenium-optically active phosphine complex catalyst (Patent Document 2).

(iii) A process to anti-selectively synthesize an optically active β-hydroxy-α-phthalimidocarboxylic acid ester by asymmetrically hydrogenating a racemic β-keto-α-phthalimidocarboxylic acid ester with catalytic asymmetric hydrogenation reaction using a ruthenium-optically active phosphine complex catalyst (Patent Document 3).

In addition, a β-keto-α-amino-higher carboxylic acid ester having a long carbon chain is an important synthesis intermediate of a ceramide derivative useful for skin protection agents among β-keto-α-aminocarboxylic acid esters. The following processes are conventionally known as processes for producing a β-keto-α-amino-higher carboxylic acid ester.

(iv) A process to obtain methyl β-keto-α-acetylaminooctadecanoate by homologation of palmitoyl chloride with methyl acetoacetate; and then, diazonizing the product by a phenyldiazonium salt; and reducing the diazo group with zinc (Patent Document 1).

(v) A method containing steps of oximating methyl β-keto-hexadecanoate with sodium nitrite; acetylating the hydroxyl group of the oxime; and successively reducing the oxime position by hydrogenation reaction (Patent Document 4).

Patent Document 1: JP 2976214 B
Patent Document 2: WO2005/005371
Patent Document 3: WO2005/069930
Patent Document 4: JP 2733583 B

DISCLOSURE OF THE INVENTION

Problems to be Solved by the Invention

However, syn-form is selectively obtained in the method (i); therefore, an extra step is required for inverting the steric configuration of the hydroxy group.

In the method (ii), the α-amino group of the β-keto-α-aminocarboxylic acid ester as a raw material is not allowed to have a substituent group and the synthesis method is limited, although the anti-form can be directly obtained. Further, the method (ii) cannot be widely applied, since the chemical structure of the raw material which can exhibit high steric selectivity is limited.

There is a problem in terms of safety in the method (iii), since hazardous hydrogen gas is used at high pressure. Further, the method (iii) is not industrially advantageous, since an expensive optically active phosphine ligand is used. Furthermore, the method (iii) cannot be widely applied, since chemical structure of the raw material is limited.

The method (iv) involves a large number of steps and is thus complicated. Further, the method (iv) is not industrially advantageous, since an explosive diazo compound has to be used as an intermediate compound.

The method (v) also involves a large number of steps and is thus complicated. Further, there is a problem in terms of safety and the method is not industrially advantageous, since hazardous hydrogen gas is used.

Means for Solving the Problems

The present inventors made various investigations to solve the above-mentioned problems; and consequently completed a process for directly and selectively producing an anti-form of optically active β-hydroxy-α-aminocarboxylic acid ester by asymmetric reduction of a β-keto-α-aminocarboxylic acid ester using a prescribed optically active amine complex as a catalyst.

The present invention relates to a process for producing an optically active β-hydroxy-α-aminocarboxylic acid ester;

comprising a step of asymmetric reduction reaction of a β-keto-α-aminocarboxylic acid ester represented by the general formula (2):

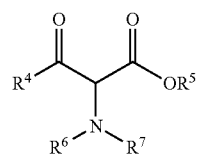

(2)

wherein, $R^4$ is a hydrogen atom, an optionally substituted alkyl group having 1 to 21 carbon atoms, an optionally substituted alkenyl group having 2 to 21 carbon atoms, an optionally substituted alkynyl group having 2 to 21 carbon atoms, an optionally substituted aralkyl group having 7 to 20 carbon atoms, or an optionally substituted aryl group having 6 to 20 carbon atoms; $R^5$ is an optionally substituted alkyl group having 1 to 10 carbon atoms, an optionally substituted aralkyl group having 7 to 20 carbon atoms, or an optionally substituted aryl group having 6 to 20 carbon atoms; $R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl group having 1 to 40 carbon atoms, or an amino-protecting group; $R^6$ and $R^7$ may constitute a heterocycle together with the neighboring nitrogen atom,
in the presence of an optically active amine complex represented by the general formula (1):

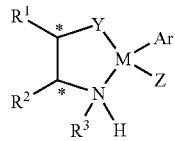

(1)

wherein, * indicates an asymmetric carbon atom; $R^1$ and $R^2$ each may be the same or different, and is an optionally substituted alkyl group having 1 to 21 carbon atoms, an optionally substituted aralkyl group having 7 to 20 carbon atoms, or an optionally substituted aryl group having 6 to 20 carbon atoms; further, $R^1$ and $R^2$ may constitute a ring; $R^3$ is a hydrogen atom, an optionally substituted alkyl group having 1 to 21 carbon atoms, an optionally substituted aralkyl group having 7 to 20 carbon atoms, or an optionally substituted aryl group having 6 to 20 carbon; Ar is an optionally substituted aromatic compound; M is a transition metal; Z is a halogen atom, an optionally substituted alkylsulfonyloxy group, an optionally substituted arylsulfonyloxy group, or an optionally substituted aralkylsulfonyloxy group; and Y is an oxygen atom, an optionally substituted alkylsulfonylamide group, an optionally substituted arylsulfonylamide group, or an optionally substituted aralkylsulfonylamide group,
and hydrogen or a hydrogen donor compound;
wherein, the optically active β-hydroxy-α-aminocarboxylic acid ester is represented by the following general formula (3) or general formula (4):

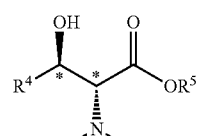

(3)

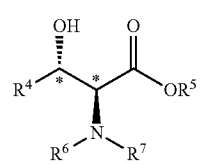

(4)

wherein, * indicates an asymmetric carbon atom; $R^4$, $R^5$, $R^6$ and $R^7$ are the same as described above.

Further, the present invention relates to a process for producing the β-keto-α-aminocarboxylic acid ester represented by the formula (2);
comprising a step of reacting a glycine derivative represented by the general formula (5):

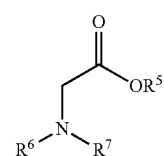

(5)

wherein, $R^5$ is an optionally substituted alkyl group having 1 to 10 carbon atoms, an optionally substituted aralkyl group having 7 to 20 carbon atoms, or an optionally substituted aryl group having 6 to 20 carbon atoms; $R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl group having 1 to 40 carbon atoms, or an amino-protecting group; and $R^6$ and $R^7$ may constitute a heterocycle together with the neighboring nitrogen atom,
with a carboxylic acid derivative represented by the general formula (6):

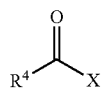

(6)

wherein, X is a halogen atom, an optionally substituted acyloxy group, an optionally substituted alkyloxycarbonyloxy group, an optionally substituted sulfonyloxy group, an optionally substituted alkyloxy group, an optionally substituted aryloxy group, or an optionally substituted imidazole group; and $R^4$ is hydrogen atom, an optionally substituted alkyl group having 1 to 21 carbon atoms, an optionally substituted alkenyl group having 2 to 21 carbon atoms, an optionally substituted alkynyl group having 2 to 21 carbon atoms, an optionally substituted aralkyl group having 7 to 20 carbon atoms, or an optionally substituted aryl group having 6 to 20 carbon atoms,
in the presence of a Lewis acid and an amine.

Furthermore, the present invention relates to a β-keto-α-stearoylaminooctadecanoic acid ester represented by the general formula (15):

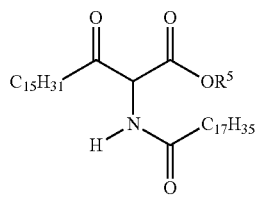

(15)

wherein, $R^5$ is an optionally substituted alkyl group having 1 to 10 carbon atoms, an optionally substituted aralkyl group having 7 to 20 carbon atoms, or an optionally substituted aryl group having 6 to 20 carbon atoms.

EFFECT OF THE INVENTION

An anti-form of an optically active β-hydroxy-α-aminocarboxylic acid ester can be efficiently, simply and industrially advantageously produced by the process of the present invention.

BEST MODE FOR CARRYING OUT THE INVENTION

Hereinafter, the present invention is described more in detail.
In the specification, examples of the substituent groups on function groups constituting $R^1$ to $R^8$, X, Y, Z, Ar and M include an alkyl group, an aryl group, an aralkyl group, an amino group, a nitro group, a sulfonyl group, a halogen atom, a hydroxyl group, an acyloxy group, an alkoxy group and the like; however, the substituent group is not limited to the examples.

First, a step is described, in which a glycine derivative represented by the general formula (5):

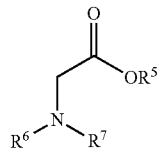

(5)

is reacted with a carboxylic acid derivative represented by the general formula (6):

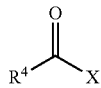

(6)

in the presence of a Lewis acid and an amine to produce a β-keto-α-aminocarboxylic acid ester represented by the general formula (2):

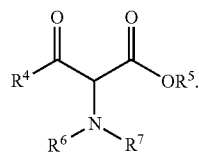

(2)

In the above general formula (6), $R^4$ is a hydrogen atom, an optionally substituted alkyl group having 1 to 21 carbon atoms, an optionally substituted alkenyl group having 2 to 21 carbon atoms, an optionally substituted alkynyl group having 2 to 21 carbon atoms, an optionally substituted aralkyl group having 7 to 20 carbon atoms, or an optionally substituted aryl group having 6 to 20 carbon atoms.

Examples of an optionally substituted alkyl group having 1 to 21 carbon atoms include a methyl group, an ethyl group, a propyl group, an isopropyl group, an isobutyl group, a tert-butyl group, a cyclopentyl group, a cyclohexyl group, a pentadecyl group, a 1-hydroxypentadecyl group, a dodecyl group and the like.

Examples of an optionally substituted alkenyl group having 2 to 21 carbon atoms include a vinyl group, an allyl group, a trans-1-pentadecenyl group, a 3-hydroxy-trans-1-pentadeceyl group and the like. Examples of an optionally substituted alkynyl group having 2 to 21 carbon atoms include a 1-pentadecynyl group and the like.

Examples of an optionally substituted aralkyl group having 7 to 20 carbon atoms include a benzyl group and the like.

Examples of an optionally substituted aryl group having 6 to 20 carbon atoms include a phenyl group, a p-methoxyphenyl group, a p-chlorophenyl group, a p-nitrophenyl group, a p-tolyl group, a naphthyl group and the like.

Among the examples, an optionally substituted alkyl group having 10 to 21 carbon atoms, an optionally substituted alkenyl group having 10 to 21 carbon atoms, and an optionally substituted alkynyl group having 10 to 21 carbon atoms are preferable, and an optionally substituted alkyl group having 11 to 21 carbon atoms, an optionally substituted alkenyl group having 11 to 21 carbon atoms, and an optionally substituted alkynyl group having 11 to 21 carbon atoms are more preferable, as $R^4$ in terms of usability of the compound (2). Especially, a pentadecyl group, a 1-hydroxypentadecyl group, a trans-1-pentadecenyl group, and a 1-pentadecynyl group are preferable.

In the above formula (6), X is a halogen atom, an optionally substituted acyloxy group, an optionally substituted alkyloxycarbonyloxy group, an optionally substituted sulfonyloxy group, an optionally substituted alkyloxy group, an optionally substituted aryloxy group, or an optionally substituted imidazole group.

Specific examples include halogen atoms such as a fluorine atom, a chlorine atom, a bromine atom and an iodine atom; acyloxy groups such as an acetyloxy group, a trichloroacetyloxy group and a pivaloyloxy group; alkyloxycarbonyloxy groups such as a methoxycarbonyloxy group, an ethoxycarbonyloxy group, an isopropyloxycarbonyloxy group and an isobutyloxycarbonyloxy group; sulfonyloxy groups such as a methanesulfonyloxy group and a p-toluenesulfonyloxy group; alkyloxy groups such as a methoxy group, an ethoxy group and a benzyloxy group; aryloxy groups such as a phenyloxy group and a p-nitrophenyloxy group; and imidazole groups such as an imidazole group and a N-methylimidazole group.

Among the examples, a chlorine atom, a bromine atom, a methoxy group, an ethoxy group, a methoxycarbonyloxy group, an ethoxycarbonyloxy group, a trichloroacetyloxy group, a pivaloyloxy group and a N-methylimidazole group are preferable in terms of economic efficiency and yield. A chlorine atom is particularly preferable.

In the above formula (5), $R^5$ is an optionally substituted alkyl group having 1 to 10 carbon atoms, an aralkyl group having 7 to 20 carbon atoms, or an optionally substituted aryl group having 6 to 20 carbon atoms.

Examples of an optionally substituted alkyl group having 1 to 10 carbon atoms include a methyl group, an ethyl group, a propyl group, an isopropyl group, an isobutyl group, a tert-butyl group and the like. Specific examples of an optionally substituted aralkyl group having 7 to 20 carbon atoms and an optionally substituted aryl group having 6 to 20 carbon atoms include ones described above. Among the examples, a methyl group, an ethyl group, an isopropyl group and a benzyl group are preferable, and an ethyl group is more preferable, in terms of easiness of raw material synthesis and easiness of deesterification reaction.

$R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl having 1 to 40 carbon atoms, or an amino-protecting group.

Specific examples of an optionally substituted alkyl group having 1 to 10 carbon atoms, the optionally substituted aralkyl group having 7 to 20 carbon atoms and the optionally substituted aryl group having 6 to 20 carbon atoms include ones described above.

Examples of an optionally substituted acyl having 1 to 40 carbon atoms include a formyl group, an acetyl group, a trifluoroacetyl group, a trichloroacetyl group, a chloroacetyl group, a benzoyl group, an octadecanoyl group, a 2-hydroxyoctadecanoyl group, a 2-oxooctadecanoyl group, a docosanoyl group, a 2-hydroxdocosanoyl group, a 30-(8,11-icosadienoyloxy)triacontanoyl group and the like.

Examples of an amino-protecting group include protective groups described in "Protective Groups in Organic Synthesis 3rd ed. (Theodora W. Greene and Peter G. M. Wuts Ed., Wiley-Interscience; New York, 1999)" excluding the above-mentioned optionally substituted alkyl group having 1 to 10 carbon atoms, optionally substituted aralkyl group, optionally substituted aryl group having 6 to 20 carbon atoms and optionally substituted acyl having 1 to 40 carbon atoms.

Among the examples, preferable are alkoxycarbonyl groups such as a methoxycarbonyl group, an ethoxycarbonyl group, a benzyloxycarbonyl group and a tert-butoxycarbonyl group, and sulfonyl groups such as a p-nitrobenzenesulfonyl group which are easy to be deprotected.

$R^6$ and $R^7$ may constitute a heterocycle together with the neighboring nitrogen atom. A phthaloyl group may be exemplified as such a functional group.

It is preferable as a definition of $R^6$ and $R^7$ that one of $R^6$ and $R^7$ is an optionally substituted acyl group having 1 to 40 carbon atoms, an optionally substituted aralkyl group having 7 to 20 carbon atoms, or an alkoxycarbonyl group having 1 to 21 carbon atoms and the other is hydrogen; or $R^6$ and $R^7$ constitute a heterocycle together with the neighboring nitrogen atom.

It is more preferable that one of $R^6$ and $R^7$ is an optionally substituted acyl group having 1 to 40 carbon atoms and the other is hydrogen. In such a case, a formyl group, an acetyl group, a benzoyl group, an octadecanoyl group, a 2-hydroxyoctadecanoyl group, a 2-oxooctadecanoyl group, a docosanoyl group, a 2-hydroxydocosanoyl group and a 30-(8,11-icosadienoyloxy)triacontanoyl are preferable, and an octadecanoyl group is particularly preferable, as an optionally substituted acyl group having 1 to 40 carbon atoms in terms of easiness of deprotection and usability of the compound.

The compound represented by the general formula (15):

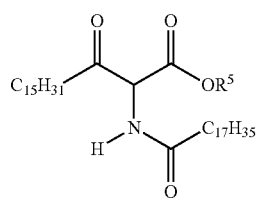

(15)

corresponding to the produced compound (2) wherein $R^4$ is a pentadecyl group, $R^6$ and $R^7$ are a octadecanoyl group and a hydrogen atom, is a novel compound found by the present inventors and is an important synthetic intermediate for ceramides useful as cosmetic components. In the above formula (15), $R^5$ is the same as described above, and a methyl group or an ethyl group is preferable.

The amount of the carboxylic acid derivative (6) to be used in the step is not particularly limited; however, the amount is generally 0.1 to 10 equivalent and preferably 0.5 to 3 equivalent, relative to the glycine derivative (5). If the carboxylic acid derivative (6) is more economical than the glycine derivative (5), it is preferable that the use amount of the carboxylic acid derivative (6) is larger; and if the carboxylic acid derivative (6) is more expensive than the glycine derivative (5), it is preferable that the use amount of the carboxylic acid derivative (6) is less.

An amine to be used in the step is not particularly limited, and examples thereof include secondary amines such as diethylamine, diisopropylamine and diisobutylamine; and tertiary amines such as trimethylamine, triethylamine, tributylamine and diisopropylethylamine. Among the examples, triethylamine, tributylamine and diisopropylethylamine are preferable in terms of yield.

The amount of an amine to be used in the step is not particularly limited; however, the amount is generally 0.5 to 10 equivalent and preferably 1 to 5 equivalent, relative to the glycine derivative (5).

A Lewis acid to be used in the step is not particularly limited; and examples thereof include titanium tetrachloride, trichloroisopropyloxytitanium, titanium tetrabromide, zirconium tetrachloride, hafnium tetrachloride, aluminum chloride, iron trichloride, antimony chloride, tin tetrachloride, tin triflate and the like. Among the examples, titanium tetrachloride is preferable in terms of yield.

The amount of a Lewis acid to be used in the step is not particularly limited; however, the amount is generally 0.5 to 10 equivalent and preferably 1 to 5 equivalent, relative to the glycine derivative (5).

It is preferable in the step to add an N-methylimidazole derivative at the time of the reaction depending on the substrate. Examples of the N-methylimidazole derivative to be added include N-methylimidazole, 2-methyl-N-methylimidazole, 2-ethyl-N-methylimidazole and 2-isopropyl-N-methylimidazole. Among the examples, N-methylimidazole is preferable in terms of economic efficiency.

In case the N-methylimidazole derivative is used in the step, the use amount is not particularly limited; however, the amount is generally 0.5 to 10 equivalent, preferably 1 to 3 equivalent and more preferably 1 to 1.5 equivalent, relative to the carboxylic acid derivative (6).

A reaction solvent to be used in the step is not particularly limited as long as the solvent does not inhibit the reaction; and examples thereof include hydrocarbon solvents such as pentane, hexane, heptane, cyclohexane, methylcyclohexane and petroleum ethers; ester solvents such as ethyl acetate and methyl acetate; aromatic hydrocarbon solvents such as toluene, chlorobenzene, benzene and xylene; nitrile solvents such as acetonitrile and propionitrile; ether solvents such as tert-butyl methyl ether, diethyl ether, diisopropyl ether, tetrahydrofuran and dioxane; amide solvents such as N,N-dimethylformamide and N,N-dimethylacetamide; sulfoxide solvents such as dimethyl sulfoxide; halogenated hydrocarbon solvents such as methylene chloride, 1,2-dichloroethane, chloroform and carbon tetrachloride. Among the examples, hexane, cyclohexane, methylcyclohexane, toluene, chlorobenzene, methylene chloride and 1,2-dichloroethane are preferable. Two or more of the solvents may be used in the form of a mixture. In case of using a solvent mixture, the mixing ratio is not particularly limited.

A concentration of the carboxylic acid derivative (6) at the time of the reaction differs in accordance with a reaction solvent to be used; however, the reaction can be carried out generally in 1 to 50% (w/v) and preferably in 2 to 30% (w/v).

A reaction temperature differs in accordance with the kinds and use amounts of the glycine derivative (5), the carboxylic acid derivative (6), a Lewis acid and an amine in addition to the kind of a reaction solvent to be used; however, the temperature is generally in a range of the melting point or higher and the boiling point or lower of the reaction solvent to be used. It is preferable to carry out the reaction at higher temperature in order to complete the reaction within a short time, and it is preferable to carry out the reaction at temperature set to be low in order to suppress side reaction. The temperature is generally −100 to 100° C. and furthermore preferably −50 to 40° C.

A reaction time differs in accordance with the kinds and use amounts of the glycine derivative (5), the carboxylic acid derivative (6), a Lewis acid, an amine and an N-methylimidazole derivative, the kind of a reaction solvent to be used, and a reaction temperature; however, the reaction time is generally about 1 to 24 hours when the reaction temperature is −50 to 40° C.

A mixing order of the glycine derivative (5), the carboxylic acid derivative (6), a Lewis acid, an amine, an N-methylimidazole derivative, a reaction solvent and the like to be used in the step is arbitrary, and is not particularly limited; however, it is preferable to add the carboxylic acid derivative (6) to a mixture of the glycine derivative (5) and the N-methylimidazole derivative and further add the Lewis acid and the amine thereto.

A step is described, in which a compound (9):

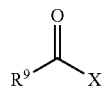
(9)

corresponding to the above formula (6) wherein $R^4$ is an optionally substituted alkyl group having 11 to 21 carbon atoms, an optionally substituted alkenyl group having 11 to 21 carbon atoms, or an optionally substituted alkynyl group having 11 to 21 carbon atoms, is used to carry out the reaction to produce a β-keto-α-aminocarboxylic acid ester represented by the general formula (10):

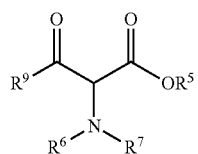
(10)

$R^5$ to $R^7$ in the above formulae (9) and (10) are the same as described above; $R^9$ is an optionally substituted alkyl group having 11 to 21 carbon atoms, an optionally substituted alkenyl group having 11 to 21 carbon atoms, or an optionally substituted alkynyl group having 11 to 21 carbon atoms, in the reaction of the step.

Also in the step, the reaction may be carried out by the above-mentioned method; however, it is preferable in the reaction to use economical N-methylimidazole as an N-methylimidazole derivative in order to promote the reaction at high yield. A reaction temperature is preferably −50° C. or higher, more preferably −40° C. or higher, and particularly preferably −20° C. or higher. Further, it is preferable to use chlorobenzene as a solvent.

A common treatment for obtaining a product from a reaction mixture may be carried out as a post-treatment of the reaction. For example, water, hydrochloric acid, alkaline water or the like may be added to a reaction mixture after the reaction, and extraction operation may be carried out by using a common extraction solvent such as ethyl acetate, diethyl ether, methylene chloride, toluene and hexane. The objective product can be obtained by removing a reaction solvent and an extraction solvent from an obtained extract in reduced pressure. The product obtained in such a manner may be subjected to a common purification such as silica gel chromatography, distillation, recrystallization or the like to further improve the purity, if necessary.

Next, a step is described, in which asymmetric reduction reaction of a β-keto-α-aminocarboxylic acid ester represented by the above formula (2) is carried out in the presence of an optically active amine complex represented by the general formula (1):

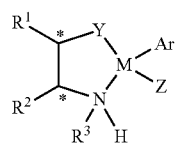
(1)

together with hydrogen or a hydrogen donor compound, to produce an optically active β-hydroxy-α-aminocarboxylic acid ester represented by the general formula (3) or general formula (4):

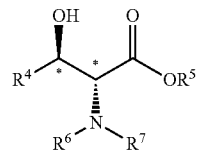
(3)

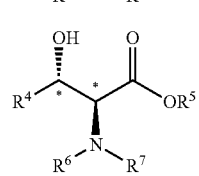
(4)

In the above formulae (2), (3) and (4), $R^4$, $R^5$, $R^6$ and $R^7$ are the same as described above.

In the above formulae (3) and (4), * indicates a symmetric carbon atom. Since the compound (3) or (4) contains two asymmetric carbon atoms, there are two kinds of diastereomers. A compound like the compound (3) or (4) having relative steric configuration is referred to as an anti-form. The other diastereomer is referred to as a syn-form, and represented by the following general formula (23) or (24):

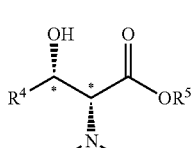
(23)

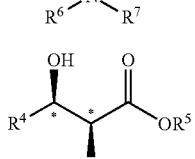
(24)

wherein * indicates an asymmetric carbon atom; and $R^4$, $R^5$, $R^6$ and $R^7$ are the same as described above. According to the present invention method, a compound represented by the above formula (3) or (4) which is an anti-form can be preferentially produced.

In case that $R^4$ is a hydrogen atom, the carbon atom substituted by the hydroxyl group at the 3-position of the compound (3) or (4) cannot be naturally an asymmetric atom. Accordingly, no diastereomer such as an anti-form or syn-form is present, since there is only one asymmetric carbon atom.

A production process of the compound (2) is not particularly limited; and the process described above may be used; and also, for example, the compound may be produced by a conventionally known method such as a method in which a β-ketoester is treated with sodium nitrite for oximation of the α-position and only the oxime is reduced by hydrogenation to form an amino group.

In the optically active amine complex (1) to be used in the step, * indicates an asymmetric carbon atom.

M is a transition metal; and examples thereof include palladium, rhodium, ruthenium, iridium, platinum, zirconium, titanium, chromium, cobalt, copper, nickel, zinc, manganese, iron, ytterbium, lanthanum and samarium. Among the examples, ruthenium, rhodium and iridium are preferable.

In the above formula (1), $R^1$ and $R^2$ each may be the same or different; and is an optionally substituted alkyl group having 1 to 21 carbon atoms, an optionally substituted aryl group having 6 to 20 carbon atoms, or an optionally substituted aralkyl group having 7 to 20 carbon atoms; and $R^1$ and $R^2$ may constitute a ring. Examples of an optionally substituted alkyl group having 1 to 21 carbon atoms, an optionally substituted aryl group having 6 to 20 carbon atoms, and an optionally substituted aralkyl group having 7 to 20 carbon atoms include ones described above; and the ring group constituted by $R^1$ and $R^2$ together may include a tetramethylene group. $R^1$ and $R^2$ are preferably phenyl or tetramethylene in terms of steric selectivity of the reaction.

$R^3$ is a hydrogen atom, an optionally substituted alkyl group having 1 to 21 carbon atoms, an optionally substituted aralkyl group having 7 to 20 carbon atoms, or an optionally substituted aryl group having 6 to 20 carbon atoms; and specific examples thereof include ones described above. A methyl group and a hydrogen atom are preferable and a hydrogen atom is particularly preferable, in terms of reaction yield and steric selectivity.

Ar is an optionally substituted aromatic compound; and examples thereof include benzene, toluene, xylene, mesitylene, hexamethylbenzene, ethylbenzene, tert-butylbenzene, p-cymene, cumene and pentamethylcyclopentadianyl. Among the examples, p-cymene, benzene and mesitylene are preferable.

Z is a halogen atom, an optionally substituted alkylsulfonyloxy group, an optionally substituted arylsulfonyloxy group, or an optionally substituted aralkylsulfonyloxy group; and examples thereof include a fluorine atom, a chlorine atom, a bromine atom, an iodine atom, a trifluoromethanesulfonyloxy group, a methanesulfonyloxy group and a p-toluenesulfonyloxy group. Among the examples, a chlorine atom and a trifluoromethanesulfonyloxy group are preferable.

Y is an oxygen atom, an optionally substituted alkylsulfonylamide group, an optionally substituted arylsulfonylamide group or an optionally substituted aralkylsulfonylamide group; and examples thereof include an oxygen atom; optionally substituted alkylsulfonylamide groups such as a methanesulfonylamide group, a trifluoromethanesulfonylamide group and a camphorsulfonylamide group; optionally substituted arylsulfonylamide groups such as a benzenesulfonylamide group, a p-toluenesulfonylamide group, a p-trifluoromethylbenzenesulfonylamide group, a p-dodecylbenzenesulfonylamide group and an o,m,p-nitrobenzenesulfonylamide group; and optionally substituted aralkylsulfonylamide groups such as a benzylsulfonylamide group. Among the examples, a p-toluenesulfonylamide group and a camphorsulfonylamide group are preferable in terms of reaction yield and steric selectivity of the reaction.

Examples of an optically active amine complex (1) include a RuCl[(R,R)-TsDPEN](p-cymene) complex, a RuCl[(S,S)-TsDPEN](p-cymene) complex, a RuOTf[(R,R)-TsDPEN](p-cymene) complex, and a RuOTf[(S,S)-TsDPEN](p-cymene) complex. The (S,S)-TsDPEN represents (1S,2S)-N-monotosyl-1,2-diphenylethylenediamine, and OTf represents a trifluoromethanesulfonyloxy group.

For example, a RuCl[(R,R)-TsDPEN](p-cymene) complex can be represented by the following formula (25):

(25)

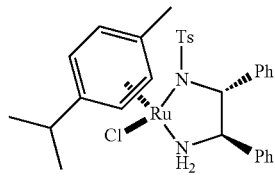

and the RuOTf[(R,R)-TsDPEN](p-cymene) complex can be represented by the following formula (26):

(26)

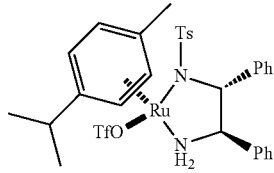

The optically active amine complex (1) can be synthesized by a method described in J. Am. Chem. Soc., 1996, 118, 2521. Further, a commercialized product may be used. The optically active amine complex (1) to be used in the step may be one prepared previously and isolated and purified, or one prepared in a reaction mixture may be directly used.

An amount of the optically active amine complex (1) to be used in the step is not particularly limited; however, the amount is generally 0.00001 to 1 equivalent and preferably 0.0001 to 0.2 equivalent, relative to a β-keto-α-aminocarboxylic acid ester represented by the above-mentioned formula (2).

Hydrogen or a hydrogen donor compound to be used in the step is not particularly limited; and examples thereof include alcohols such as methanol, ethanol, n-propanol and isopropanol; formic acid; formic acid salts such as sodium formate and ammonium formate; and hydrogen. Particularly, formic acid, sodium formate and hydrogen are preferable, and formic acid is more particularly preferable, in terms of yield.

An amount of a hydrogen donor compound to be used in the step is not particularly limited; however, the amount is generally 1 to 100 equivalent and preferably 1 to 10 equivalent, relative to a β-keto-α-aminocarboxylic acid ester represented by the above formula (4).

Further, a base may be used in the step. Examples of the base include inorganic bases such as sodium hydroxide, potassium hydroxide and potassium carbonate; alkoxides such as sodium methoxide and potassium tert-butoxide; and amines such as triethylamine, trimethylamine and ammonia. In case that formic acid is used as a hydrogen donor compound, it is preferable that a base is used, and triethylamine is particularly preferable to be used.

In case that a base is used in the step, a use amount is not particularly limited; however, the amount is generally 0.01 to 100 equivalent, preferably 0.1 to 10 equivalent and more preferably 1 to 10 equivalent, relative to a β-keto-α-aminocarboxylic acid ester represented by the above formula (2).

When a hydrogen donor compound or a base to be coexisted is in a state of a liquid, a reaction solvent is not particularly required; and it is preferable to carry out the reaction without a solvent, since the reaction can be completed within a very short time and the use amount of a catalyst can be reduced. However, a reaction solvent may be used in accordance with a reaction substrate. A reaction solvent is not particularly limited as long as the solvent does not inhibit the reaction; and examples thereof include the above-mentioned hydrocarbon solvents; ester solvents; aromatic hydrocarbon solvents; nitrile solvents; ether solvents; amide solvents; sulfoxide solvents; halogenated hydrocarbon solvents; alcohol solvents such as methanol, ethanol, isopropanol and n-butanol; carboxylic acid solvents such as formic acid and acetic acid; and water. Further, two or more of the solvents may be used in form of a mixture. In case of using a solvent mixture, the mixing ratio is not particularly limited.

A concentration of the β-keto-α-aminocarboxylic acid ester (2) at the time of carrying out the reaction differs in accordance with a reaction solvent to be used; however, the concentration is generally 1 to 50% (w/v) and preferably 4 to 30% (w/v) to carry out the reaction.

A reaction temperature differs in accordance with the kinds and use amounts of an optically active transition metal complex and a hydrogen donor compound and the kind of a reaction solvent to be used; however, the temperature is generally in a range of the melting point or higher and the boiling point or lower of a reaction solvent to be used. It is preferable to carry out the reaction at higher temperature, in order to complete the reaction within a short time; and it is preferable to carry out the reaction at temperature set to be low, in terms of suppression of side reaction. It is generally −20 to 150° C. and furthermore preferably 0 to 70° C.

A reaction time differs in accordance with the kinds and use amounts of an optically active transition metal complex and a hydrogen donor compound to be used, the kind of a reaction solvent, and a reaction temperature; however, the time is generally about 1 to 36 hours when the reaction temperature is 0 to 70° C.

A mixing order of the β-keto-α-aminocarboxylic acid ester (2), the optically active amine complex (1), hydrogen or a hydrogen donor compound, a reaction solvent and the like to be used in the step is arbitrary and is not particularly limited; however, it is preferable to add hydrogen or a hydrogen donor compound to a mixture of the β-keto-α-aminocarboxylic acid ester (2) and the optically active amine complex (1). Also when a base is added, it is preferable to add hydrogen or the hydrogen donor compound to a mixture of the β-keto-α-aminocarboxylic acid ester (2), the optically active amine complex (1) and the base. The hydrogen donor compound may be added at once for the reaction, or may be continuously or intermittently added while the reaction is promoted. If gas is generated along with the proceeding of the reaction, it is preferable to successively add the compound along with the proceeding of the reaction in terms of safety.

As a post-treatment of the reaction, a common treatment for obtaining a product from a reaction mixture may be carried out. For example, water, hydrochloric acid, alkaline water or the like may be added to a reaction mixture on completion of the reaction; and extraction operation may be carried out by using a common extraction solvent such as ethyl acetate, diethyl ether, methylene chloride, toluene and hexane. The objective product can be obtained by removing a reaction solvent and an extraction solvent from an obtained extract in reduced pressure. The product obtained in such a manner may be subjected to a common purification such as silica gel chromatography, distillation, recrystallization or the like to further improve the purity, if necessary.

Next, a step is described, in which asymmetric reduction reaction of a compound represented by the above formula (2) is carried out using a transition metal complex having an optically active phosphine ligand as a catalyst, and the steric configuration of the hydroxyl group at the 3-position is inversed, if necessary, to produce an optically active β-hydroxy-α-aminocarboxylic acid ester represented by the above general formula (3) or (4).

Examples of a transition metal in a transition metal complex having an optically active phosphine ligand to be used in the step are ones exemplified for M in the above formula (1).

An optically active phosphine ligand is not particularly limited; and examples thereof include binaphthyl type phosphine ligands represented by the general formula (16) (hereinafter, abbreviated as BINAP), biphenyl type phosphine ligands represented by the general formula (17) (hereinafter, abbreviated as MeO-BIPHEP), biphenyl type phosphine ligands represented by the general formula (18) (hereinafter, abbreviated as SEGPHOS), biphenyl type phosphine ligands represented by the general formula (19) (hereinafter, abbreviated as TUNEPHOS), bisphosphine ligands represented by the general formula (20) (hereinafter, abbreviated as DUPHOS), alkyl phosphine ligands represented by the general formula (21) (hereinafter, abbreviated as BISP), and biphenylphosphine ligands represented by the general formula (22) (hereinafter, abbreviated as DIOXANPHOS).

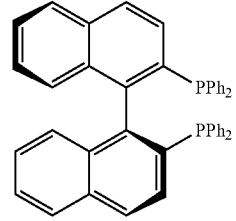

(16)

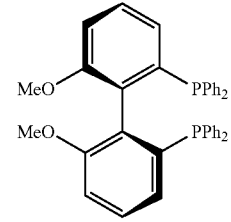

(17)

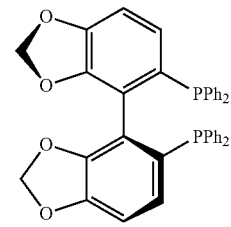

(18)

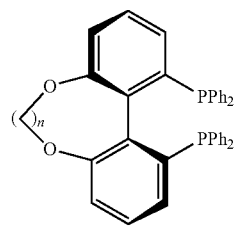

(19)

wherein, n is an integer of 1 to 6.

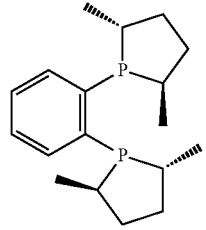

(20)

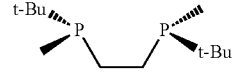

(21)

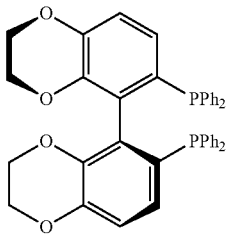
(22)

Among the examples, BINAP, DIOXANPHOS, TUNEPHOS, SEGPHOS and MeO-BIPHEP are preferable in terms of steric selectivity.

A transition metal complex having an optically active phosphine ligand to be used in the step can be prepared by mixing a transition metal compound and an optically active phosphine ligand in a proper solvent. A complex previously prepared and isolated may be used, or a mixture prepared in a reaction mixture may be directly used.

A use amount of a transition metal complex having an optically active phosphine ligand in the step is not particularly limited; and the amount is generally 0.00001 to 1 equivalent and preferably 0.0001 to 0.2 equivalent, relative to a β-keto-α-aminocarboxylic acid ester represented by the above formula (2).

Hydrogen to be used in the step may be commonly hydrogen gas. A pressure of hydrogen gas is not particularly limited; and the pressure is generally in a range from 1 to 150 atmospheric pressure and preferably in a range from 5 to 100 atmospheric pressure. It is preferable to carry out the reaction at an increased pressure, in order to complete the reaction in a short time.

A reaction solvent to be used in the step is not particularly limited as long as the solvent does not inhibit the reaction; and examples thereof include the above-mentioned hydrocarbon solvents; ester solvents; aromatic hydrocarbon solvents; nitrile solvents; ether solvents; amide solvents; sulfoxide solvents; halogenated hydrocarbon solvents; alcohol solvents; carboxylic acid solvents; and water. Two or more of solvents may be used in form of a mixture. In case of using a solvent mixture, a mixing ratio is not particularly limited.

A concentration of the β-keto-α-aminocarboxylic acid ester (2) at the time of carrying out the reaction differs in accordance with a reaction solvent to be used; however, the concentration is generally 1 to 50% (w/v) and preferably 4 to 30% (w/v) to carry out the reaction.

A reaction temperature differs in accordance with the kind and use amount of an optically active transition metal complex having an optically active phosphine ligand, the kind of a reaction solvent to be used, and hydrogen pressure; and the temperature is generally in a range of the melting point or higher and the boiling point or lower of a reaction solvent to be used. It is preferable to carry out the reaction at higher temperature in order to complete the reaction within a short time; and it is preferable to carry out the reaction at temperature set to be low in terms of suppression of side reaction. The temperature is generally −20 to 150° C. and furthermore preferably 0 to 100° C.

A reaction time differs in accordance with the kind and use amount of an optically active transition metal complex having an optically active phosphine ligand, a hydrogen pressure, the type of a reaction solvent to be used, and a reaction temperature; however, the time is generally about 1 to 36 hours when a reaction temperature is 0 to 100° C.

A mixing order of the β-keto-α-aminocarboxylic acid ester (2), a transition metal complex having an optically active phosphine ligand, a hydrogen gas, a reaction solvent and the like to be used in the reaction is arbitrary, and the order is not particularly limited; however, a hydrogen gas may be added to a mixture of the β-keto-α-aminocarboxylic acid ester (2) and a transition metal complex having an optically active phosphine ligand.

As a post-treatment of the reaction, a common treatment for obtaining a product from a reaction mixture may be carried out. For example, a reaction solvent may be simply removed from a reaction mixture. Otherwise, water, hydrochloric acid, alkaline water or the like may be added to a reaction mixture on completion of the reaction, and extraction operation may be carried out by using a common extraction solvent such as ethyl acetate, diethyl ether, methylene chloride, toluene and hexane. The objective product can be obtained by removing a reaction solvent and an extraction solvent from an obtained extracted solution in reduced pressure. The product obtained in such a manner may be subjected to a common purification such as silica gel chromatography, distillation, recrystallization or the like to further improve the purity, if necessary.

Such a syn-form represented by the above formula (23) or (24), not such an anti-form represented by the above (3) or (4), can be produced in some cases by asymmetric hydrogenation in the step in accordance with the kinds of the β-keto-α-aminocarboxylic acid ester (2) and a transition metal complex having an optically active phosphine ligand to be used. When a syn-form is produced, the steric configuration of the hydroxyl group at the 3-position may be inversed to convert the syn-form to the anti-form, if necessary.

A method for inversing the steric configuration of the hydroxyl group at the 3-position is not particularly limited; for example, a method of converting $R^6$ or $R^7$ of the compound (23) or (24) to an acyl group such as an acetyl group or an octadecanoyl group as necessary and then allowing thionyl chloride to act is exemplified.

A use amount of thionyl chloride at the time is not particularly limited; however the amount is generally 1 to 50 equivalent and preferably 1 to 10 equivalent, relative to the compound (23) or (24).

A solvent to be used in an inverse operation is not particularly limited as long as the solvent does not inhibit the reaction. Examples thereof include hydrocarbon solvents; ester solvents; aromatic hydrocarbon solvents; nitrile solvents; ether solvents; amide solvents; sulfoxide solvents; halogenated hydrocarbon solvents; and thionyl chloride. Among the examples, hexane, cyclohexane, methylcyclohexane, toluene, chlorobenzene, methylene chloride, tetrahydrofuran and thionyl chloride are preferable. Two or more of solvents may be used in form of a mixture. In case of using a solvent mixture, the mixing ratio is not particularly limited.

A concentration of the compound (23) or (24) at the time of carrying out an inverse operation differs in accordance with a reaction solvent to be used; however, the concentration is generally 1 to 50% (w/v) and preferably 4 to 30% (w/v) to carry out the reaction.

A reaction temperature during an inverse operation differs in accordance with the kind of the compound (23) or (24), a use amount of thionyl chloride and the kind of a reaction solvent to be used; however, the temperature is generally in a range of the melting point or higher and the boiling point or lower of a reaction solvent to be used. It is preferable to carry out the reaction at higher temperature in order to complete the reaction within a short time, and it is preferable to carry out the reaction at temperature set to be low in terms of suppression of side reaction. The temperature is generally −40 to 100° C. and furthermore preferably −10 to 50° C.

A reaction time of an inverse operation differs in accordance with the kind of the compound (23) and (24), a use amount of thionyl chloride, the kind of a reaction solvent and a reaction temperature; however, the time is generally about 1 to 24 hours when the reaction temperature is −10 to 50° C.

A mixing order of the compound (23) or (24), thionyl chloride, a reaction solvent and the like to be used for an inversion operation is arbitrary and is not particularly limited.

As a post-treatment of the reaction, a common treatment for obtaining a product from a reaction mixture may be carried out. For example, water, hydrochloric acid, alkaline water or the like may be added to a reaction mixture on completion of the reaction, and extraction operation may be carried out by using a common extraction solvent such as ethyl acetate, diethyl ether, methylene chloride, toluene and hexane. The objective product can be obtained by removing a reaction solvent and an extraction solvent from an obtained extract in reduced pressure. The product obtained in such a manner may be subjected to a common purification such as silica gel chromatography, distillation, recrystallization or the like to further improve the purity, of necessary.

Next, a step is described, in which the ester part of an optically active β-hydroxy-α-aminocarboxylic acid ester produced above and represented by the above (3) or (4) is reduced, and an amino-substituent group is converted into an acyl group if necessary, to produce an optically active 2-amino-1,3-diol derivative represented by the general formula (7) or the general formula (8):

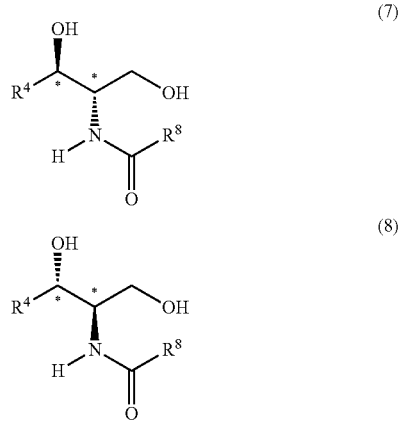

$R^4$ in an optically active 2-amino-1,3-diol derivative (7) or (8) is the same as described above.

$R^8$ is an optionally substituted alkyl group or an alkanoyl group, having 11 to 40 carbon atoms; and examples thereof include a pentadecyl group, a heptadecyl group, a 1-hydroxyheptadecyl group, a 1-oxoheptadecyl group, a henicosyl group, a 1-hydroxyhenicosyl group and a 29-(8,11-icosadienoyloxy)nonacosyl group. Among the example, a heptadecyl group, a 1-hydroxyheptadecyl group, a 1-oxoheptadecyl group, a henicosyl group, a 1-hydroxyhenicosyl group and a 29-(8,11-icosadienoyloxy)nonacosyl group are preferable in term of usability as a ceramide derivative.

The term, "an amino-substituent group is converted into an acyl group if necessary", means that $R^6$ and $R^7$ of the amino-substituent group in the compound (3) or (4) may be converted into an acyl group and hydrogen, respectively, or may not be converted. In case that one of $R^6$ and $R^7$ in the compound (3) or (4) is hydrogen, the substituent group excluding hydrogen may be eliminated and converted into an acyl group; and when both of $R^6$ and $R^7$ are substituent groups and not hydrogen, both amino substituent groups are eliminated and one of them may be converted into an acyl group.

In case that one of $R^6$ and $R^7$ in the compound (3) or (4) is an acyl group and the other is hydrogen, the compound (7) or (8) can be obtained, even if the amino substituent group is not converted into an acyl group; however, the acyl group of $R^6$ or $R^7$ may be eliminated and converted into a different acyl group. Further, a step of converting an amino-substituent group to an acyl group may be carried out, for example, by performing elimination reaction of the amino substituent group after reduction of the ester part of the compound (3) or (4) and finally performing acylation reaction of the unsubstituted amino group, or by performing acylation reaction of the unsubstituted amino group after an elimination reaction of the amino substituent group and finally reducing the ester part.

At first, a method for reducing the ester part of the compound (3) or (4) or a compound obtained by converting the amino substituent group of the compound (3) or (4) into an acyl group is described.

A reducing agent for reducing the ester part is not particularly limited; and examples thereof include sodium borohydride, lithium borohydride, lithium aluminum hydride, borane, disobutylaluminum hydride and hydrogen. Among the examples, sodium borohydride is preferable in terms of economic efficiency.

An amount of a reducing agent to be used in a reduction reaction is not particularly limited; however, the amount is generally 0.5 to 10 equivalent and preferably 1 to 3 equivalent, relative to an optically active β-hydroxy-α-aminocarboxylic acid ester (3) or (4) or a compound obtained by converting the amino substituent group of the compound (3) or (4) into an acyl group.

It is preferable to use sodium borohydride as a reducing agent, since the reaction may be activated and/or epimeration during the reaction may be suppressed when the reduction is carried out in the presence of a Lewis acid.

A Lewis acid is not particularly limited; and examples thereof include titanium tetrachloride, tin tetrachloride, boron trifluoride diethyl ether complex, zinc chloride, zinc bromide, zinc iodide, magnesium chloride, magnesium bromide, magnesium iodide, aluminum chloride, lithium chloride, lithium bromide, calcium chloride, iron chloride and nickel chloride. Among the example, calcium chloride is preferable in terms of economic efficiency.

A use amount of a Lewis acid to be coexisted is not particularly limited; however, the amount is generally 0.5 to 10 equivalent and preferably 1 to 3 equivalent, relative to an optically active β-hydroxy-α-aminocarboxylic acid ester (3) or (4) or a compound obtained by converting the amino-substituent group of the compound (3) or (4) into an acyl group.

A reaction solvent to be used in the step is not particularly limited as long as the solvent does not inhibit the reaction; and examples thereof include the above-mentioned hydrocarbon solvents; ester solvents; aromatic hydrocarbon solvents; nitrile solvents; ether solvents; amide solvents; sulfoxide solvents; halogenated hydrocarbon solvents; alcohol solvents such as methanol, ethanol, isopropanol and n-butanol; and water. Among the examples, chlorobenzene, n-butanol, tetrahydrofuran and dioxane are preferable. Two or more of solvents may be used in form of a mixture. In case of using a solvent mixture, a mixing ratio is not particularly limited.

A concentration of a compound to be subjected to a reduction reaction differs in accordance with a reaction solvent to be used; however, the concentration is generally 1 to 50% (w/v) and preferably 4 to 30% (w/v) to carry out the reaction.

A reaction temperature differs in accordance with a compound to be subjected to the reduction reaction, the kind and use amount of a reducing agent, and the kind of a reaction solvent; however, the temperature is generally in a range of the melting point or higher and the boiling point or lower of a reaction solvent to be used. It is preferable to carry out the reaction at higher temperature in order to complete the reaction within a short time, and it is preferable to carry out the reaction at temperature set to be low in terms of suppression of side reaction. The temperature is generally −70 to 120° C. and furthermore preferably 0 to 100° C.

A reaction time differs in accordance with a compound to be subjected to a reduction reaction, the kind and use amount of a reducing agent, the kind of a reaction solvent, and a reaction temperature; however, the time is generally about 1 to 24 hours when the reaction temperature is 0 to 100° C.

A mixing order of a compound to be subjected to a reduction reaction, a reducing agent, a reaction solvent and the like is arbitrary and is not particularly limited.

As a post-treatment of the reaction, a common treatment for obtaining a product from a reaction mixture may be carried out. For example, water, hydrochloric acid, alkaline water or the like may be added to a reaction mixture after the reaction, and an extraction operation may be carried out by using a common extraction solvent such as ethyl acetate, diethyl ether, methylene chloride, toluene and hexane. The objective product can be obtained by removing a reaction solvent and an extraction solvent from an obtained extract in reduced pressure. The product obtained in such a manner may be subjected to a common purification such as silica gel chromatography, distillation, recrystallization or the like to further improve the purity, if necessary.

Next, a step of converting an amino-substituent group into an acyl group when necessary is described. The conversion reaction into an acyl group may be carried out generally by eliminating the substituent group of an amino group to give an unsubstituted amino group and then N-acylating the amino group with an acylation agent.

An elimination reaction of an amino substituent group differs depending on the substituent group, and may be deprotection reaction described in "Protective Groups in Organic Synthesis 3rd ed. (Theodora W. Greene and Peter G. M. Wuts, Ed., Wiley-Interscience: New York, 1999)" in case of an amino-protecting group. For example, when an amino substituent group is an acetyl group or a methoxycarbonyl group, the substituent group can be eliminated by an acid or a base; and in case of a phthaloyl group, the substituent group can be eliminated by acid hydrolysis or treatment with methylamine or hydrazine. In case of a benzyloxycarbonyl group or a benzyl group, the substituent group can be eliminated by hydrogenolysis.

An acylation reaction of an unsubstituted amino group is carried out using an acylation agent. Examples of the acylation agent to be used include acid chlorides such as stearoyl chloride, pivaloyl chloride, docosanoic acid chloride and 30-(8,11-icosadienoyloxy)triacontanoic acid chloride; esters such as methyl stearate, methyl 2-hydroxystearate, methyl 2-oxostearate, methyl docosanoate and methyl 2-hydroxydocosanoate. Further, the acylation reaction may be carried out using acid anhydrides or mixed anhydrides of a corresponding carboxylic acid.

A use amount of an acylation agent to be used in an acylation reaction is not particularly limited; however, the amount is generally 0.5 to 10 equivalent and preferably 1 to 2 equivalent, relative to an optically active β-hydroxy-α-aminocarboxylic acid ester (3) or (4) or an ester part-reduced compound thereof.

A base may be used in an acylation reaction, if necessary; and examples of the base to be used include the above-mentioned inorganic bases and organic bases such as triethylamine, pyridine and 4-dimethylaminopyridine.

A use amount of a base to be used in an acylation reaction is not particularly limited; however, the amount is generally 0.01 to 10 equivalent and preferably 0.01 to 2 equivalent, relative to an optically active β-hydroxy-α-aminocarboxylic acid ester (3) or (4) or an ester part-reduced compound thereof.

A reaction solvent to be used in the reaction is not particularly limited as long as the solvent does not inhibit the reaction; and examples thereof include hydrocarbon solvents; ester solvents; aromatic hydrocarbon solvents; nitrile solvents; ether solvents; amide solvents; sulfoxide solvents; halogenated hydrocarbon solvents; alcohol solvents; and water. Among the examples, chlorobenzene, methylene chloride, n-butanol, tetrahydrofuran and dioxane are preferable. Two or more of solvents may be used in form of a mixture. In case of using a solvent mixture, a mixing ratio is not particularly limited.

A concentration of an optically active β-hydroxy-α-aminocarboxylic acid ester (3) or (4) or an ester part-reduced compound thereof at the time of the reaction differs in accordance with a reaction solvent to be used; however, the concentration is generally 1 to 50% (w/v) and preferably 4 to 30% (w/v) to carry out the reaction.

A reaction temperature differs in accordance with an optically active β-hydroxy-α-aminocarboxylic acid ester (3) or (4) or an ester part-reduced compound thereof to be used, the kind and use amount of an acylation agent, and the kind of a reaction solvent; however, the temperature is generally in a range of the melting point or higher and the boiling point or lower of a reaction solvent to be used. It is preferable to carry out the reaction at higher temperature in order to complete the reaction within a short time, and it is preferable to carry out the reaction at temperature set to be low in terms of suppression of side reaction. The temperature is generally −50 to 120° C. and furthermore preferably 0 to 100° C.

A reaction time differs in accordance with an optically active β-hydroxy-α-aminocarboxylic acid ester (3) or (4) or an ester part-reduced compound thereof to be used, the kind and use amount of an acylation agent, and the type of a reaction solvent, and a reaction temperature; however, the time is generally about 1 to 24 hours when the reaction temperature is 0 to 100° C.

A mixing order of an optically active β-hydroxy-α-aminocarboxylic acid ester (3) or (4) or an ester part-reduced compound thereof, an acylation agent and a reaction solvent to be used in the reaction is arbitrary, and is not particularly limited.

As a post-treatment of the reaction, a common treatment for obtaining a product from a reaction mixture may be carried out. For example, water, hydrochloric acid, alkaline water or the like may be added to a reaction mixture on completion of the reaction, and an extraction operation may be carried out by using a common extraction solvent such as ethyl acetate, diethyl ether, methylene chloride, toluene and hexane. The objective product can be obtained by removing a reaction solvent and an extraction solvent from an obtained extract in reduced pressure. The product obtained in such a manner may be subjected to a common purification such as silica gel chromatography, distillation, recrystallization or the like to further improve the purity, if necessary.

EXAMPLES

Hereinafter, the present invention is described with reference to examples; however, it is not intended that the present invention be limited to the illustrated examples.

Example 1

Production of ethyl 2-acetylamino-3-oxooctadecanoate

A methylene chloride solution (5.0 ml) of N-acetylglycine ethyl ester (72.5 mg, 0.50 mmol) and N-methylimidazole (50.4 mg, 0.61 mmol) was cooled to −45° C., and a methylene chloride solution (0.5 ml) of palmitoyl chloride (142.6 mg, 0.50 mmol) was added thereto in nitrogen atmosphere. After the mixture was stirred for 20 minutes at the same temperature, a methylene chloride solution (0.5 ml) of titanium tetrachloride (340.4 mg, 1.78 mmol) and a methylene chloride solution (0.5 ml) of tributylamine (372.4 mg, 2.01 mmol) were added thereto. The resulting mixture was stirred for 2 hours at −45° C. Water was added thereto, and the mixture was heated to room temperature, and the organic layer was separated. Further, the water layer was extracted twice with methylene chloride, and the organic layers were combined and dried with magnesium sulfate. After the solvent was removed in reduced pressure, the obtained crude product was purified by silica gel chromatography (Kieselgel 60 manufactured by Merck, hexane:ethyl acetate=3:2) to obtain the title compound (148.8 mg, yield: 88%).

$^1$H NMR (400 MHz, CDCl$_3$/ppm): δ0.88(t, 3H), 1.25-1.36 (m, 29H), 2.07(s, 3H), 2.71(m, 2H), 4.26(q, 2H), 5.23(d, 1H), 6.62(d, 1H)

Example 2

Production of ethyl 2-acetylamino-3-oxooctadecanoate

A dichloromethane solution (45.0 ml) of N-acetylglycine ethyl ester (1.50 g, 10.33 mmol) and N-methylimidazole (1.02 mg, 12.40 mmol) was cooled to −45° C., and palmitoyl chloride (2.84 g, 10.33 mmol) was added thereto in nitrogen atmosphere. After the mixture was stirred for 20 minutes at the same temperature, titanium tetrachloride (6.86 mg, 36.16 mmol) and triethylamine (4.18 g, 41.31 mmol) were added thereto. The resulting mixture was stirred for 2 hours at −45° C. Water (20 mL) was added thereto, and the mixture was heated to room temperature, and the organic layer was separated. It was confirmed by comparative analysis with sample product using HPLC that the organic layer contained 2.81 g of the title compound (yield: 71%).

Example 3

Production of ethyl 2-acetylamino-3-oxooctadecanoate

A toluene solution (33.0 ml) of N-acetylglycine ethyl ester (1.00 g, 6.89 mmol) and N-methylimidazole (679 mg, 8.27 mmol) was cooled to −20° C., and palmitoyl chloride (1.89 g, 6.89 mmol) was added thereto in nitrogen atmosphere. After the mixture was stirred for 30 minutes at the same temperature, titanium tetrachloride (4.57 mg, 24.12 mmol) and triethylamine (2.79 g, 27.56 mmol) were added thereto. The resulting mixture was stirred for 2 hours at −20° C. Water (20 mL) was added thereto, and the mixture was heated to room temperature, and the organic layer was separated. It was confirmed by comparative analysis with sample product using HPLC that the organic layer contained 1.75 g of the title compound (yield: 66%).

Example 4

Production of ethyl 2-acetylamino-3-oxooctadecanoate

A chlorobenzene solution (45.0 ml) of N-acetylglycine ethyl ester (1.50 g, 10.33 mmol) and N-methylimidazole (1.02 g, 12.40 mmol) was cooled to −20° C., and palmitoyl chloride (2.84 g, 10.33 mmol) was added thereto in nitrogen atmosphere. After the mixture was stirred for 45 minutes at the same temperature, titanium tetrachloride (6.86 mg, 36.16 mmol) and triethylamine (4.18 g, 41.31 mmol) were added thereto. The resulting mixture was stirred for 2 hours at −20° C. Water (20 mL) was added thereto, and the mixture was heated to room temperature, and the organic layer was separated. It was confirmed by comparative analysis with sample product using HPLC that the organic layer contained 2.92 g of the title compound (yield: 74%).

Example 5

Production of ethyl 2-acetylamino-3-oxooctadecanoate

A chlorobenzene solution (45.0 ml) of N-acetylglycine ethyl ester (1.50 g, 10.33 mmol) and N-methylimidazole (1.02 g, 12.40 mmol) was cooled to −10° C., and palmitoyl chloride (2.84 g, 10.33 mmol) was added thereto in nitrogen atmosphere. After the mixture was stirred for 45 minutes at the same temperature, titanium tetrachloride (6.86 mg, 36.16 mmol) and triethylamine (4.18 g, 41.31 mmol) were added thereto. The resulting mixture was stirred for 2 hours at −10° C. Water (20 mL) was added thereto, and the mixture was heated to room temperature, and the organic layer was separated. It was confirmed by comparative analysis with sample product using HPLC that the organic layer contained 2.92 g of the title compound (yield: 80%).

Example 6

Production of ethyl 2-acetylamino-3-oxooctadecanoate

A chlorobenzene solution (45.0 ml) of N-acetylglycine ethyl ester (1.50 g, 10.33 mmol) and N-methylimidazole (1.02 g, 12.40 mmol) was cooled to −10° C., and palmitoyl chloride (2.84 g, 10.33 mmol) was added thereto in nitrogen atmosphere. After the mixture was stirred for 45 minutes at the same temperature, titanium tetrachloride (6.86 mg, 36.16 mmol) and tributylamine (7.66 g, 41.32 mmol) were added thereto. The resulting mixture was stirred for 2 hours at −10° C. Water (20 mL) was added thereto, and the mixture was heated to room temperature, and the organic layer was separated. It was confirmed by comparative analysis with sample product using HPLC that the organic layer contained 3.33 g of the title compound (yield: 84%).

Example 7

Production of ethyl 2-acetylamino-3-oxooctadecanoate

A chlorobenzene solution (45.0 ml) of N-acetylglycine ethyl ester (1.50 g, 10.33 mmol) and N-methylimidazole (1.02 g, 12.40 mmol) was cooled to 0° C., and palmitoyl chloride (2.84 g, 10.33 mmol) was added thereto in nitrogen atmosphere. After the mixture was stirred for 25 minutes at the same temperature, titanium tetrachloride (6.86 mg, 36.16 mmol) and triethylamine (4.18 g, 41.31 mmol) were added thereto. The resulting mixture was stirred for 2 hours at 0° C. Water (20 mL) was added thereto, and the mixture was heated to room temperature, and the organic layer was separated. It was confirmed by comparative analysis with sample product using HPLC that the organic layer contained 2.93 g of the title compound (yield: 74%).

Example 8

Production of ethyl 2-formylamino-3-oxooctadecanoate

A methylene chloride solution (100 ml) of N-formylglycine ethyl ester (1.31 g, 10 mmol) and N-methylimidazole (985.4 mg, 12 mmol) was cooled to −45° C., and a methylene chloride solution (10 ml) of palmitoyl chloride (2.85 mg, 10 mmol) was added thereto in nitrogen atmosphere. After the mixture was stirred for 20 minutes at the same temperature, a methylene chloride solution (10 ml) of titanium tetrachloride (6.78 mg, 35 mmol) and a methylene chloride solution (10 ml) of tributylamine (7.42 g, 40 mmol) were added thereto. The resulting mixture was stirred for 3 hours at −45° C. After 100 ml of water was added thereto, and the mixture was heated to room temperature, and the organic layer was separated. Further, the water layer was extracted twice with methylene chloride. The organic layers were combined and dried with magnesium sulfate. After the solvent was removed in reduced pressure, the obtained crude product was purified by silica gel chromatography (Kieselgel 60 manufactured by Merck, solely ethyl acetate) to obtain the title compound (3.15 mg, yield: 85%).

$^1$H NMR (400 MHz, CDCl$_3$/ppm): δ0.88(t, 3H), 1.25-1.33 (m, 29H), 2.73(m, 2H), 4.26(q, 2H), 5.28(d, 1H), 6.78(bs, 1H), 8.25(s, 1H)

Example 9

Production of ethyl 2-octadecanoylamino-3-oxooctadecanoate

A methylene chloride solution (100 ml) of N-octadecanoylglycine ethyl ester (3.70 g, 10 mmol) and N-methylimidazole (985.4 mg, 12 mmol) was cooled to −45° C., and a methylene chloride solution (10 ml) of palmitoyl chloride (2.76 mg, 9.74 mmol) was added thereto in nitrogen atmosphere. After the mixture was stirred for 20 minutes at the same temperature, a methylene chloride solution (10 ml) of titanium tetrachloride (6.81 mg, 35 mmol) and a methylene chloride solution (10 ml) of tributylamine (7.42 g, 40 mmol) were added thereto. The resulting mixture was stirred for 2 hours at −45° C. After 100 ml of water was added thereto and the mixture was heated to room temperature, the organic layer was separated. Further, the water layer was extracted twice with methylene chloride (100 ml), and the organic layers were combined and dried with magnesium sulfate. After the solvent was removed in reduced pressure, the obtained crude product was purified by silica gel chromatography (Kieselgel 60 manufactured by Merck, hexane:ethyl acetate=4:1) to obtain the title compound (3.20 mg, yield: 54%).

$^1$H NMR (400 MHz, CDCl$_3$/ppm): δ0.88(m, 6H), 1.25-1.32(m, 59H), 2.27(t, 2H), 2.70(m, 2H), 4.25(m, 2H), 5.22(d, 1H), 6.58(d, 1H)

Example 10

Production of ethyl 2-octadecanoylamino-3-oxooctadecanoate

A chlorobenzene solution (33.0 ml) of N-octadecanoylglycine ethyl ester (2.00 g, 5.41 mmol) and N-methylimidazole (533 mg, 6.49 mmol) was cooled to −10° C., and palmitoyl chloride (1.49 g, 5.41 mmol) was added thereto in nitrogen atmosphere. After the mixture was stirred for 45 minutes at the same temperature, titanium tetrachloride (3.60 g, 18.94 mmol) and tributylamine (4.01 g, 21.64 mmol) were added thereto. The resulting mixture was stirred for 1.5 hours at −10° C. After water (25 ml) was added thereto and the mixture was heated to room temperature, the organic layer was separated. It was confirmed by comparative analysis with sample product using HPLC that the organic layer contained 2.52 g of the title compound (yield: 77%).

Example 11

Production of methyl 2-octadecanoylamino-3-oxooctadecanoate

The title compound (yield: 36%) was obtained in the same manner as Example 9, except that N-octadecanoylglycine methyl ester is used instead of N-octadecanoylglycine ethyl ester in Example 9.

$^1$H NMR (400 MHz, CDCl$_3$/ppm): δ0.88(m, 6H), 1.25(m, 56H), 2.27(t, 2H), 2.70(m, 2H), 3.80(s, 3H), 5.24(d, 1H), 6.59(d, 1H)

Example 12

Production of ethyl (2R,3R)-2-acetylamino-3-hydroxyoctadecanoate

A dehydrated THF solution (0.5 ml) of triethylamine (131.9 mg, 1.30 mmol) and a dehydrated THF solution (0.5 ml) of formic acid (64.2 mg, 1.37 mmol) were added to a dehydrated THF solution (4.0 ml) of RuCl[(R,R)-TsDPEN](p-cymene) complex (19.6 mg, 0.03 mmol) and ethyl 2-acetylamino-3-oxooctadecanoate (7.70 g, 0.20 mmol) synthesized in the same method as Example 1. After the mixture was stirred for 3 days at room temperature, the reaction solvent was removed in reduced pressure. Water was added thereto, and the mixture was extracted with ethyl acetate three times. The organic layers were combined and dried with magnesium sulfate. After the solvent was removed in reduced pressure, the obtained crude product was purified by silica gel chromatography (Kieselgel 60 manufactured by Merck, solely ethyl acetate) to obtain the title compound (71.3 mg, yield: 94%). The product was analyzed by HPLC to find that anti-form: syn-form was 93:7 and the optical purity of the anti-form was 98% ee.

Herein, (R,R)-TsDPEN is (1R,2R)-N-tosyl-1,2-diphenylethylenediamine (hereinafter, the same).

$^1$H NMR (400 MHz, CDCl$_3$/ppm) of anti-form: δ0.88(t, 3H), 1.25-1.35(m, 29H), 1.43-1.49(m, 2H), 2.07(s, 3H), 3.90-97(m, 1H), 4.24(m, 2H), 4.67(dd, 1H), 6.45(d, 1H)

$^1$H NMR (400 MHz, CDCl$_3$/ppm) of syn-form: δ0.88(t, 3H), 1.25-1.35(m, 29H), 1.43-1.49(m, 2H), 2.07(s, 3H), 4.09-4.15(m, 1H), 4.24(m, 2H), 4.65(dd, 1H), 6.20(d, 1H)

Conditions of Optical Purity HPLC Analysis
  Column: CHIRALPAK AD-H
  Column temperature: 25° C.
  Moving phase: hexane/isopropanol=95/5

Flow speed: 0.5 ml/min
Detection wavelength: 210 nm
Retention time: anti-form—18.9 minutes and 24.1 minutes
syn-form—29.7 minutes and 56.6 minutes Example 13

Production of ethyl
(2R,3R)-2-acetylamino-3-hydroxyoctadecanoate

Triethylamine (1.32 g, 13.05 mmol) and formic acid (350 mg, 7.82 mmol) were added to a chlorobenzene solution (10.0 ml) of RuCl[(R,R)-TsDPEN](p-cymene) complex (17.6 mg, 0.03 mmol) and ethyl 2-acetylamino-3-oxooctadecanoate (1.00 g, 2.61 mmol) synthesized in the same method as Example 1. After the reaction mixture was stirred for 15.5 hours at 40° C., water (10 mL) was added thereto and separation operation was carried out at 40° C. to obtain the organic layer. It was confirmed by comparative analysis of the organic layer with sample product using HPLC that the organic layer contained 0.96 g of the title compound (yield: 96%). Further, anti-form:syn-form was 95:5 and the optical purity of the anti-form was 97% ee.

Example 14

Production of ethyl
(2R,3R)-2-acetylamino-3-hydroxyoctadecanoate

Triethylamine (1.32 g, 13.05 mmol) and formic acid (350 mg, 7.82 mmol) were added to a chlorobenzene solution (10.0 ml) of RuCl[(R,R)-TsDPEN](p-cymene) complex (8.8 mg, 0.01 mmol) and ethyl 2-acetylamino-3-oxooctadecanoate (1.00 g, 2.61 mmol) synthesized in the same method as Example 1. After the reaction mixture was stirred for 3 days at 40° C., water (10 mL) was added thereto and separation operation was carried out at 40° C. to obtain the organic layer. It was confirmed by comparative analysis of the organic layer with sample product using HPLC that the organic layer contained 0.96 g of the title compound was contained (yield: 96%). Further, anti-form:syn-form was 98:2 and the optical purity of the anti-form was 97% ee.

Example 15

Production of ethyl
(2R,3R)-2-formylamino-3-hydroxyoctadecanoate

A dehydrated THF solution (0.5 ml) of triethylamine (131.7 mg, 1.30 mmol) and a dehydrated THF solution (0.5 ml) of formic acid (64.2 mg, 1.37 mmol) were added to a dehydrated THF solution (4.0 ml) of RuCl[(R,R)-TsDPEN](p-cymene) complex (19.6 mg, 0.03 mmol) and ethyl 2-formylamino-3-oxooctadecanoate (73.5 mg, 0.20 mmol) synthesized in the same method as Example 8. After the mixture was stirred for 3 days at room temperature, the reaction solvent was removed in reduced pressure. Water was added thereto and extraction with ethyl acetate was carried out three times. The organic layers were combined and dried with magnesium sulfate. After the solvent was removed in reduced pressure, the obtained crude product was purified by silica gel chromatography (Kieselgel 60 manufactured by Merck, hexane:ethyl acetate=1:2) to obtain the title compound (64.6 mg, yield: 87%). The product was analyzed by HPLC to find that anti-form:syn-form was 95:5 and the optical purity of the anti-form was 96% ee.

$^1$H NMR (400 MHz, CDCl$_3$/ppm) of anti-form: δ0.88(t, 3H), 1.25-1.38(m, 29H), 1.43-1.58(m, 2H), 3.95(m, 1H), 4.23(m, 2H), 4.73(dd, 1H), 6.61(d, 1H), 8.24(s, 1H)
$^1$H NMR (400 MHz, CDCl$_3$/ppm) of syn-form: δ0.88(t, 3H), 1.25-1.38(m, 29H), 1.43-1.58(m, 2H), 3.95(m, 1H), 4.23(m, 2H), 4.73(dd, 1H), 6.52(d, 1H), 8.31(s, 1H)
Conditions of Optical Purity HPLC Analysis
  Column: CHIRALPAK AD-H, two columns
  Column temperature: 25° C.
  Moving phase: hexane/isopropanol=9/1
  Flow speed: 0.5 ml/min
  Detection wavelength: 210 nm
  Retention time: anti-form—22.2 minutes and 24.3 minutes
  syn-form—39.2 minutes and 40.3 minutes Example 16

Production of ethyl
(2R,3R)-2-octadecanoylamino-3-hydroxyoctadecanoate

A methylene chloride solution (0.5 ml) of triethylamine (131.6 mg, 1.30 mmol) and a methylene chloride solution (0.5 ml) of formic acid (64.5 mg, 1.37 mmol) were added to a methylene chloride solution (4.0 ml) of RuCl[(R,R)-TsDPEN](p-cymene) complex (18.9 mg, 0.03 mmol) and ethyl 2-octadecanoylamino-3-oxooctadecanoate (121.6 mg, 0.20 mmol) synthesized in the same method as Example 9. After the mixture was stirred for 16 hours at room temperature, water was added thereto and extraction with methylene chloride was carried out three times. After the organic layers were combined and dried with magnesium sulfate, the solvent was removed in reduced pressure. The obtained crude product was purified by silica gel chromatography (Kieselgel 60 manufactured by Merck, hexane:ethyl acetate=4:1) to obtain the title compound (109.6 mg, yield: 90%). The product was analyzed by HPLC to find that anti-form:syn-form was 91:9 and the optical purity of the anti-form was 95% ee.

$^1$H NMR (400 MHz, CDCl$_3$/ppm) of anti-form: δ0.88(t, 6H), 1.25-1.40(m, 59H), 1.43-1.58(m, 2H), 2.27(t, 2H), 3.94(m, 1H), 4.23(m, 2H), 4.66(dd, 1H), 6.43(d, 1H)
$^1$H NMR (400 MHz, CDCl$_3$/ppm) of syn-form: δ0.88(t, 6H), 1.25-1.40(m, 59H), 1.43-1.58(m, 2H), 2.27(t, 2H), 4.12(m, 1H), 4.23(m, 2H), 4.66(dd, 1H), 6.15(d, 1H)
Conditions of Optical Purity HPLC Analysis
  Column: SUMICHIRAL OA-4700
  Column temperature: 25° C.
  Moving phase: hexane/isopropanol=98/2
  Flow speed: 0.5 ml/min
  Detection wavelength: 210 nm
  Retention time: anti-form—16.6 minutes and 18.9 minutes
  syn-form—25.9 minutes and 34.2 minutes Example 17

Production of ethyl
(2R,3R)-2-octadecanoylamino-3-hydroxyoctadecanoate

Triethylamine (830 mg, 8.20 mmol) and formic acid (227 mg, 4.93 mmol) were added to a chlorobenzene solution (15.0 ml) of RuCl[(R,R)-TsDPEN](p-cymene) complex (11.0 mg, 0.03 mmol) and ethyl 2-octadecanoylamino-3-oxooctadecanoate (1.00 g, 1.64 mmol) synthesized in the same method as Example 10. After the reaction mixture was stirred for 3 days at 40° C., water (10 mL) was added thereto and separation operation was carried out at 40° C. to obtain the organic layer. After the organic layer was concentrated until the total amount became 3.11 g, 10 mL of AcOEt was added thereto and recrystallization was carried out to obtain 0.73 g of the title compound (yield: 74%). Anti-form:syn-form was 100:0 and the optical purity of the anti-form was 100% ee.

Example 18

Production of ethyl (2R,3R)-2-amino-3-hydroxyoctadecanoate hydrochloride

Ethyl (2R, 3R)-2-acetylamino-3-hydroxyoctadecanoate (1.00 g, 2.59 mmol) synthesized in the same method as Example 13 was suspended in an ethanol solution of about 30 wt % of hydrogen chloride, and the mixture was stirred for 15.5 hours in refluxing condition. After ethanol (10.0 mL) was added thereto, the mixture was cooled to 26° C. The precipitated solid was filtered to obtain 0.61 g of the title compound (yield: 62%).

$^1$H NMR (400 MHz, DMSO-d6/ppm): δ1.16(t, 3H), 1.53-1.61(m, 29H), 1.71-1.79(m, 2H), 4.26(br, 1H), 4.27(s, 1H), 4.44-4.59(m, 2H), 5.91(d, 1H), 8.61(br, 2H)

Example 19

Production of ethyl (2R,3R)-2-octadecanoylamino-3-hydroxyoctadecanoate

Stearoyl chloride (227 mg, 4.93 mmol) was added to a THF solution (5.0 mL) of ethyl (2R,3R)-2-amino-3-hydroxyoctadecanoate hydrochloride (300 mg, 0.79 mmol) synthesized in the same method as Example 18 and triethylamine (239 mg, 2.37 mmol) at 27° C. After the reaction mixture was stirred at 60° C. for 3 hours, water (5 mL) and AcOEt (5 mL) were added thereto and separation operation was carried out to obtain the organic layer. The organic layer was concentrated to obtain 0.48 g of a crude product containing the title compound (rough yield: 100%).

Example 20

Production of (2R,3R)-2-octadecanoylaminooctadecane-1,3-diol

Sodium borohydride (18.6 mg, 0.50 mmol) was added to a THF (5.0 mL) solution of ethyl (2R,3R)-2-octadecanoylamino-3-hydroxyoctadecanoate (150 mg, 0.25 mmol) synthesized in the same method as Example 19 at 60° C. After the reaction mixture was stirred at 60° C. for 2.5 hours, water (1.5 mL) and AcOEt (5 mL) were added thereto and separation operation was carried out to obtain the organic layer. After the organic layer was washed with water (1.5 mL×2 times), the organic layer was concentrated.

Recrystallization in EtOH was carried out to obtain 76 mg of the title compound (yield: 55%). HPLC analysis was carried out to find that anti-form:syn-form was 92:8 and the optical purity of the anti-form was 99% ee.

$^1$H NMR (400 MHz, CDCl$_3$-DMSO-d$_6$/ppm): δ0.88(t, 3H), 1.18-1.29(m, 54H), 1.45-1.52(m, 2H), 1.61-1.65(m, 2H), 2.22(dd, 2H), 3.65-3.68(m, 2H), 3.81-3.93(m, 1H), 6.64(d, 1H)

Conditions of Optical Purity HPLC Analysis
  Column: SUMICHIRAL OA-4700
  Column temperature: 25° C.
  Moving phase: hexane/isopropanol=98/2
  Flow speed: 1.0 ml/min
  Detection wavelength: 210 nm Retention time: anti-form—32.3 minutes and 37.1 minutes
syn-form—19.1 minutes and 23.1 minutes Example 21

Production of methyl 2-octadecanoylamino-3-oxooctadecanoate

The title compound (yield: 64%) was obtained in the same manner as Example 10, except that N-octadecanoylglycine methyl ester is used instead of N-octadecanoylglycine ethyl ester in Example 10.

Example 22

Production of (2S,3R)-2-octadecanoylaminooctadecane-1,3-diol

A t-butyl methyl ether suspension (2 mL) containing ethyl (2R,3R)-2-octadecanoylamino-3-hydroxyoctadecanoate (100 mg. 0.16 mmol) synthesized in the same method as Example 17 and sodium borohydride (20.3 mg, 0.54 mmol) was stirred at 23° C. for 48 hours. After water (5 mL) was added thereto, the reaction mixture was separated at 40° C. to separate the organic layer. It was confirmed by comparative analysis of the obtained organic layer with sample product using HPLC that the organic layer contained 86.6 mg of the title compound (yield: 93%). HPLC analysis was carried out to find that anti-form:syn-form was 93:7 and the optical purity of the anti-form was 100% ee.

Example 23

Production of (2S,3R)-2-octadecanoylaminooctadecane-1,3-diol

The title compound (yield: 87%) was obtained in the same manner as Example 22, except that ethanol was used as a solvent instead of t-butyl methyl ether in Example 22. HPLC analysis was carried out to find that anti-form:syn-form was 88:12 and optical purity of the anti-form was 99% ee.

Example 24

Production of (2S,3R)-2-acetylaminooctadecane-1,3-diol

An ethanol suspension (3 mL) containing ethyl (2R,3R)-2-acetylamino-3-hydroxyoctadecanoate (68.9 mg. 0.18 mmol) synthesized in the same method as Example 14 and sodium borohydride (21.1 mg, 0.53 mmol) was stirred at 23° C. or 21 hours. After ethyl acetate and water were added thereto, the reaction mixture was stirred at 60° C. for 1 hour. After the organic layer was separated, the organic layer was washed with saturated brine and dried with magnesium sulfate. The solvent was removed in reduced pressure. It was found that 54.0 mg of the title compound was contained (yield: 88%). HPLC analysis was carried out to find that the optical purity of the anti-form was 99% ee.

$^1$H NMR (400 MHz, CDCl$_3$-CD$_3$OD/ppm): δ0.88(t, 3H), 1.18-1.30(m, 26H), 1.45-1.52(m, 2H), 2.03(s, 3H), 3.65-3.70(m, 2H), 3.73-3.80(m, 1H), 3.85-3.95(m, 1H), 6.93(d, 1H)

Conditions of Optical Purity HPLC Analysis
  Column: CHIRALPAK AD-H
  Column temperature: 25° C.
  Moving phase: hexane/isopropanol=95/5
  Flow speed: 0.5 ml/min Detection wavelength: 210 nm
Retention time: anti-form—13.7 minutes and 18.4 minutes
syn-form—11.2 minutes and 12.7 minutes

Example 25

Production of
(2S,3R)-2-acetylaminooctadecane-1,3-diol

A THF suspension (0.3 mL) containing sodium borohydride (38.2 mg, 0.93 mmol) was heated to 60° C., and a THF solution (2.5 mL) of ethyl (2R,3R)-2-acetylamino-3-hydroxyoctadecanoate (250.1 mg. 0.62 mmol) synthesized in the same manner as Example 14 was added thereto dropwise for 5.5 hours. After completion of the dropwise addition, the mixture was further stirred at 60° C. for 17 hours. After ethyl acetate and water were added thereto, the reaction mixture was stirred at 60° C. for 1 hour. After the organic layer was separated, the organic layer was washed with saturated brine and dried with magnesium sulfate. The solvent was removed in reduced pressure. It was confirmed that 178.7 mg of the title compound was contained (yield: 84%). HPLC analysis was carried out to find that the optical purity of the anti-form was 99% ee.

Example 26

Production of
(2S,3R)-2-octadecanoylaminooctadecane-1,3-diol

A THF suspension (2 mL) containing sodium borohydride (39.2 mg, 0.96 mmol) was heated to 60° C., and ethyl (2R,3R)-2-octadecanoylamino-3-hydroxyoctadecanoate (300.0 mg, 0.49 mmol) synthesized in the same manner as Example 17 was added for 2.5 hours. After completion of the dropwise addition, the mixture was further stirred at 60° C. for 24 hours. After ethyl acetate and water were added thereto, the reaction mixture was stirred at 60° C. for 1 hour. After the organic layer was separated, the obtained organic layer was washed with saturated brine and dried with magnesium sulfate. The solvent was removed in reduced pressure. It was confirmed that 219.4 mg of the title compound was contained (yield: 78%). HPLC analysis was carried out to find that anti-form:syn-form was 81:19 and the optical purity of the anti-form was 99% ee.

Example 27

Production of
(2S,3R)-2-octadecanoylaminooctadecane-1,3-diol

Ethyl (2R,3R)-2-octadecanoylamino-3-hydroxyoctadecanoate (1.50 g, 2.46 mmol) synthesized in the same manner as Example 17 was added to a THF suspension (15 mL) containing sodium borohydride (271.9 mg, 7.38 mmol) at room temperature for 0.5 hours. After completion of the dropwise addition, aluminum chloride (984.0 mg, 7.38 mmol) was added for 1 hour. After water was added to the reaction mixture, concentrated hydrochloric acid was added thereto to adjust pH of the mixture to be 1.5. The resulting reaction mixture was further stirred at 50° C. for 1 hour, and the organic layer was separated. It was confirmed by comparative analysis of the organic layer with sample product using HPLC that the organic layer contained 1.18 g of the title compound (yield: 84%). It was also found that anti-form:syn-form was 98:2 and the optical purity of the anti-form was 97% ee.

Example 28

Production of
(2S,3R)-2-octadecanoylaminooctadecane-1,3-diol

Ethyl (2R,3R)-2-octadecanoylamino-3-hydroxyoctadecanoate (5.00 g, 8.17 mmol) synthesized in the same manner as Example 17 was added to a THF suspension (48 mL) containing sodium borohydride (0.62 mg, 16.34 mmol) at 0° C. for 5 hour. After completion of the dropwise addition, calcium chloride (1.82 mg, 16.40 mmol) was added for 1 hour. After water was added to the reaction mixture, concentrated hydrochloric acid was added thereto to adjust pH of the mixture to be 1.5. The mixture was further stirred at 50° C. for 1 hour, and the organic layer was separated. It was confirmed by comparative analysis of the organic layer with sample product using HPLC that the organic layer contained 4.41 g of the title compound (yield: 95%). It was also found that anti-form:syn-form was 98:2 and the optical purity of the anti-form was 99% ee.

The invention claimed is:
1. A process for producing an optically active β-hydroxy-α-aminocarboxylic acid ester;
comprising a step of asymmetric reduction reaction of a β-keto-α-aminocarboxylic acid ester represented by the general formula (2):

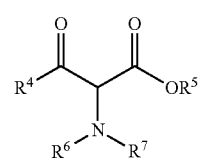

(2)

wherein, $R^4$ is a hydrogen atom, an optionally substituted alkyl group having 1 to 21 carbon atoms, an optionally substituted alkenyl group having 2 to 21 carbon atoms, an optionally substituted alkynyl group having 2 to 21 carbon atoms, or an optionally substituted aralkyl group having 7 to 20 carbon atoms; $R^5$ is an optionally substituted alkyl group having 1 to 10 carbon atoms, an optionally substituted aralkyl group having 7 to 20 carbon atoms, or an optionally substituted aryl group having 6 to 20 carbon atoms; $R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl group having 1 to 40 carbon atoms, or an amino-protecting group; $R^6$ and $R^7$ may constitute a heterocycle together with the neighboring nitrogen atom,
in the presence of an optically active amine complex represented by the general formula (1):

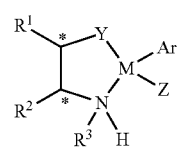

(1)

wherein, * indicates an asymmetric carbon atom; $R^1$ and $R^2$ each may be the same or different, and is an optionally substituted alkyl group having 1 to 21 carbon atoms, an optionally substituted aralkyl group having 7 to 20 carbon atoms, or an optionally substituted aryl group having 6 to 20 carbon atoms; further, $R^1$ and $R^2$ may constitute a ring; $R^3$ is a hydrogen atom, an optionally substituted alkyl group having 1 to 21 carbon atoms, an optionally substituted aralkyl group having 7 to 20 carbon atoms, or an optionally substituted aryl group having 6 to 20 carbon; Ar is an optionally substituted aromatic compound; M is a transition metal; Z is a halogen atom, an optionally substituted alkylsulfonyloxy group, an optionally substituted arylsulfonyloxy group, or an optionally substituted aralkylsulfonyloxy group; and Y is an oxygen atom, or =N—S(O$_2$)—R wherein R is an optionally substituted alkyl group, an optionally substituted aryl group or an optionally substituted aralkyl group, and hydrogen or a hydrogen donor compound;

wherein, the optically active β-hydroxy-α-aminocarboxylic acid ester is represented by the following general formula (3) or general formula (4):

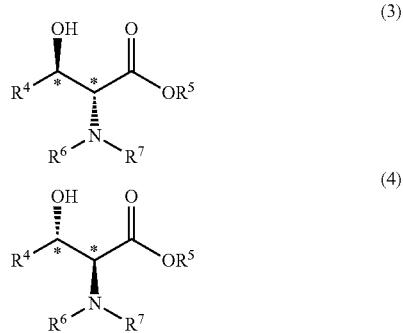

wherein, * indicates an asymmetric carbon atom unless $R^4$ is a hydrogen atom; $R^4$, $R^5$, $R^6$ and $R^7$ are the same as described above.

2. The production process according to claim 1, wherein formic acid is used as the hydrogen donor compound.

3. The production process according to claim 1, wherein the reaction is carried out in the presence of a base.

4. A process for producing a β-keto-α-aminocarboxylic acid ester;

comprising a step of reacting a glycine derivative represented by the general formula (5):

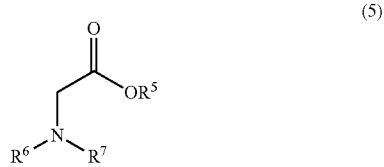

wherein, $R^5$ is an optionally substituted alkyl group having 1 to 10 carbon atoms, an optionally substituted aralkyl group having 7 to 20 carbon atoms, or an optionally substituted aryl group having 6 to 20 carbon atoms; $R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl group having 1 to 40 carbon atoms, or an amino-protecting group; and $R^6$ and $R^7$ may constitute a heterocycle together with the neighboring nitrogen atom, with a carboxylic acid derivative represented by the general formula (6):

wherein, X is a halogen atom, an optionally substituted acyloxy group, an optionally substituted alkyloxycarbonyloxy group, an optionally substituted sulfonyloxy group, an optionally substituted alkyloxy group, an optionally substituted aryloxy group, or an optionally substituted imidazole group; and $R^4$ is hydrogen atom, an optionally substituted alkyl group having 1 to 21 carbon atoms, an optionally substituted alkenyl group having 2 to 21 carbon atoms, an optionally substituted alkynyl group having 2 to 21 carbon atoms, an optionally substituted aralkyl group having 7 to 20 carbon atoms, or an optionally substituted aryl group having 6 to 20 carbon atoms, in the presence of a Lewis acid and an amine;

wherein the β-keto-α-aminocarboxylic acid ester is represented by the general formula (2):

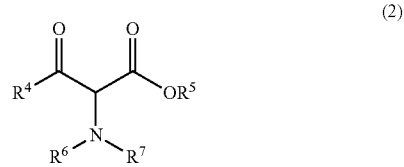

wherein, $R^4$, $R^5$, $R^6$ and $R^7$ are the same as described above.

5. The production process according to claim 4, wherein the Lewis acid is titanium tetrachloride.

6. The production process according to claim 4, wherein $R^4$ is an optionally substituted alkyl group having 11 to 21 carbon atoms, an optionally substituted alkenyl group having 11 to 21 carbon atoms, or an optionally substituted alkynyl group having 11 to 21 carbon atoms.

7. The production process according to claim 4, wherein the reaction is carried out at −40° C. or higher.

8. A process for producing an optically active β-hydroxy-α-aminocarboxylic acid ester;

comprising a step of asymmetric hydrogenation reaction of a β-keto-α-aminocarboxylic acid ester using a transition metal complex having an optically active phosphine ligand as a catalyst;

and a step of inverting the steric configuration of the hydroxyl group at the 3-position, if necessary;

wherein the optically active β-hydroxy-α-aminocarboxylic acid ester is represented by the general formula (3) or (4):

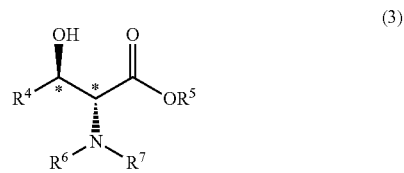

-continued (4)

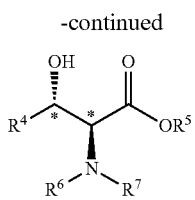

wherein, * indicates an asymmetric carbon atom unless $R^4$ is a hydrogen atom; $R^4$ is a hydrogen atom, an optionally substituted alkyl group having 1 to 21 carbon atoms, an optionally substituted alkenyl group having 2 to 21 carbon atoms, an optionally substituted alkynyl group having 2 to 21 carbon atoms, an optionally substituted aralkyl group having 7 to 20 carbon atoms, or an optionally substituted aryl group having 6 to 20 carbon atoms; $R^5$ is an optionally substituted alkyl group having 1 to 10 carbon atoms, an optionally substituted aralkyl group having 7 to 20 carbon atoms, or an optionally substituted aryl group having 6 to 20 carbon atoms; $R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl group having 1 to 40 carbon atoms, or an amino-protecting group; $R^6$ and $R^7$ may constitute a heterocycle together with the neighboring nitrogen atom, and wherein the β-keto-α-aminocarboxylic acid ester is represented by the general formula (2):

(2)

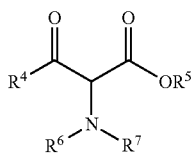

wherein, $R^4$, $R^5$, $R^6$ and $R^7$ are the same as described above, and is produced by a process comprising a step of reacting a glycine derivative represented by the general formula (5):

(5)

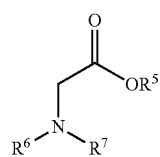

wherein, $R^5$, $R^6$ and $R^7$ are the same as described above, with a carboxylic acid derivative represented by the general formula (6):

(6)

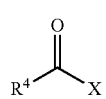

wherein, X is a halogen atom, an optionally substituted acyloxy group, an optionally substituted alkyloxycarbonyloxy group, an optionally substituted sulfonyloxy group, an optionally substituted alkyloxy group, an optionally substituted aryloxy group, or an optionally substituted imidazole group; and $R^4$ is the same as described above, in the presence of a Lewis acid and an amine.

9. A process for producing an optically active β-hydroxy-α-aminocarboxylic acid ester comprising a step of asymmetric reduction reaction of a β-keto-α-aminocarboxylic acid ester in the presence of an optically active amine complex and hydrogen or a hydrogen donor compound, wherein:

the optically active β-hydroxy-α-aminocarboxylic acid ester is represented by the following general formula (3) or general formula (4):

(3)

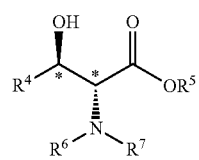

(4)

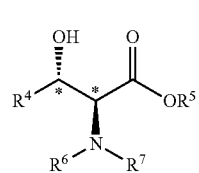

wherein, * indicates an asymmetric carbon atom unless $R^4$ is a hydrogen atom; $R^4$ is a hydrogen atom, an optionally substituted alkyl group having 1 to 21 carbon atoms, an optionally substituted alkenyl group having 2 to 21 carbon atoms, an optionally substituted alkenyl group having 2 to 21 carbon atoms, or an optionally substituted aralkyl group having 7 to 20 carbon atoms; $R^5$ is an optionally substituted alkyl group having 1 to 10 carbon atoms, an optionally substituted aralkyl group having 7 to 20 carbon atoms, or an optionally substituted aryl group having 6 to 20 carbon atoms; $R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl group having 1 to 40 carbon atoms, or an amino-protecting group; $R^6$ and $R^7$ may constitute a heterocycle together with the neighboring nitrogen atom, the β-keto-α-aminocarboxylic acid ester is represented by the general formula (2):

(2)

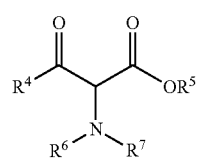

wherein $R^4$, $R^5$, $R^6$ and $R^7$ are the same as described above, and is obtained by a process comprising a step of reacting a glycine derivative represented by the general formula (5):

(5)

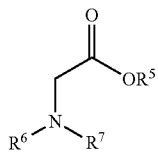

wherein, $R^5$, $R^6$ and $R^7$ are the same as described above, with a carboxylic acid derivative represented by the general formula (6):

(6)

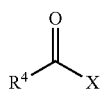

wherein, X is a halogen atom, an optionally substituted acyloxy group, an optionally substituted alkyloxycarbonyloxy group, an optionally substituted sulfonyloxy group, an optionally substituted alkyloxy group, an optionally substituted aryloxy group, or an optionally substituted imidazole group; and $R^4$ is the same as described above, in the presence of a Lewis acid and an amine, and the optically active amine complex is represented by the general formula (1):

(1)

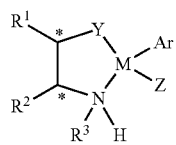

wherein, * indicates an asymmetric carbon atom; $R^1$ and $R^2$ each may be the same or different, and is an optionally substituted alkyl group having 1 to 21 carbon atoms, an optionally substituted aralkyl group having 7 to 20 carbon atoms, or an optionally substituted aryl group having 6 to 20 carbon atoms; further, $R^1$ and $R^2$ may constitute a ring; $R^3$ is a hydrogen atom, an optionally substituted alkyl group having 1 to 21 carbon atoms, an optionally substituted aralkyl group having 7 to 20 carbon atoms, or an optionally substituted aryl group having 6 to 20 carbon; Ar is an optionally substituted aromatic compound; M is a transition metal; Z is a halogen atom, an optionally substituted alkylsulfonyloxy group, an optionally substituted arylsulfonyloxy group, or an optionally substituted aralkylsulfonyloxy group; and Y is an oxygen atom, or =N—S(O$_2$)—R wherein R is an optionally substituted alkyl group, an optionally substituted aryl group or an optionally substituted aralkyl group.

10. A process for producing an optically active 2-amino-1,3-diol derivative;

comprising a step of reducing the ester part of an optically active β-hydroxy-α-aminocarboxylic acid ester;

and a step of converting the substituent group at the amino group into an acyl group if necessary;

wherein the optically active 2-amino-1,3-diol derivative is represented by the general formula (7) or general formula (8):

(7)

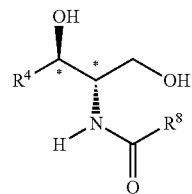

(8)

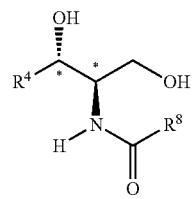

wherein, * indicates an asymmetric carbon atom unless $R^4$ is a hydrogen atom; $R^4$ is a hydrogen atom, an optionally substituted alkyl group having 1 to 21 carbon atoms, an optionally substituted alkenyl group having 2 to 21 carbon atoms, an optionally substituted alkynyl group having 2 to 21 carbon atoms, or an optionally substituted aralkyl group having 7 to 20 carbon atoms; and $R^8$ is an optionally substituted alkyl group or an alkanoyl group, having 11 to 40 carbon atoms, and wherein the optically active β-hydroxy-α-aminocarboxylic acid ester is produced by a process comprising a step of asymmetric reduction reaction of a β-keto-α-aminocarboxylic acid ester represented by the general formula (2):

(2)

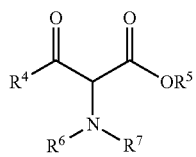

wherein, $R^4$ is the same as described above; $R^5$ is an optionally substituted alkyl group having 1 to 10 carbon atoms, an optionally substituted aralkyl group having 7 to 20 carbon atoms, or an optionally substituted aryl group having 6 to 20 carbon atoms; $R^6$ and $R^7$ each may be the same or different, and is a hydrogen atom, an optionally substituted alkyl group having 1 to 10 carbon atoms, an optionally substituted aralkyl group having 7 to 20 carbon atoms, an optionally substituted aryl group having 6 to 20 carbon atoms, an optionally substituted acyl group having 1 to 40 carbon atoms, or an amino-protecting group; $R^6$ and $R^7$ may constitute a heterocycle together with the neighboring nitrogen atom, in the presence of an optically active amine complex represented by the general formula (1):

(1)

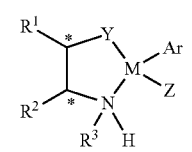

wherein, * indicates an asymmetric carbon atom; $R^1$ and $R^2$ each may be the same or different, and is an optionally substituted alkyl group having 1 to 21 carbon atoms, an optionally substituted aralkyl group having 7 to 20 carbon atoms, or an optionally substituted aryl group having 6 to 20 carbon atoms; further, $R^1$ and $R^2$ may constitute a ring; $R^3$ is a hydrogen atom, an optionally substituted alkyl group having 1 to 21 carbon atoms, an optionally substituted aralkyl group having 7 to 20 carbon atoms, or an optionally substituted aryl group having 6 to 20 carbon; Ar is an optionally substituted aromatic compound; M is a transition metal; Z is a halogen atom, an optionally substituted alkylsulfonyloxy group, an optionally substituted arylsulfonyloxy group, or an optionally substituted aralkylsulfonyloxy group; and Y is an oxygen atom, or =N—S(O$_2$)—R wherein R is an optionally substituted alkyl group, an optionally substituted aryl group or an optionally substituted aralkyl group, and hydrogen or a hydrogen donor compound, and the optically active β-hydroxy-α-aminocarboxylic acid ester is represented by the following general formula (3) or general formula (4):

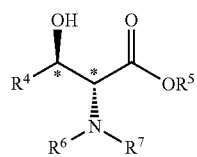
(3)

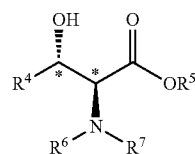
(4)

wherein, * indicates an asymmetric carbon atom unless $R^4$ is a hydrogen atom; $R^4$, $R^5$, $R^6$ and $R^7$ are the same as described above.

11. The production process according to claim 10, wherein a reducing agent for reducing the ester part is sodium borohydride.

12. The production process according to claim 11, wherein the reduction is carried out in the presence of a Lewis acid.

13. The production process according to claim 12, wherein the Lewis acid is calcium chloride.

14. The production process according to claim 1, wherein the optically active β-hydroxy-α-aminocarboxylic acid ester is in anti-form.

15. The production process according to claim 9, wherein the optically active β-hydroxy-α-aminocarboxylic acid ester is in anti-form.

* * * * *